US008697050B2

(12) United States Patent
Miyasaka et al.

(10) Patent No.: US 8,697,050 B2
(45) Date of Patent: Apr. 15, 2014

(54) METHODS OF TREATMENT USING A VECTOR ENCODING P21/$^{Cip1}$

(76) Inventors: Nobuyuki Miyasaka, Tokyo (JP); Hitoshi Kohsaka, Tokyo (JP)

(*) Notice: Subject to any disclaimer, the term of this patent is extended or adjusted under 35 U.S.C. 154(b) by 0 days.

(21) Appl. No.: 12/791,577

(22) Filed: Jun. 1, 2010

(65) Prior Publication Data
US 2010/0310508 A1 Dec. 9, 2010

Related U.S. Application Data

(63) Continuation of application No. 11/799,353, filed on May 1, 2007, now abandoned, which is a continuation of application No. 10/088,661, filed as application No. PCT/JP00/06511 on Sep. 22, 2000, now abandoned.

(30) Foreign Application Priority Data

Sep. 22, 1999 (JP) .................................. 11-269579

(51) Int. Cl.
*A01N 63/00* (2006.01)
*A01N 65/00* (2009.01)
(52) U.S. Cl.
USPC ........................................... 424/93.2; 514/44
(58) Field of Classification Search
USPC .................................. 424/93.2, 93.21; 514/44
See application file for complete search history.

(56) References Cited

U.S. PATENT DOCUMENTS

| | | | |
|---|---|---|---|
| 6,420,345 B1 | 7/2002 | Patel et al. | |
| 2003/0023034 A1 | 1/2003 | Nandabalan et al. | |

FOREIGN PATENT DOCUMENTS

| | | | |
|---|---|---|---|
| JP | 11-509739 | 8/1998 | |
| WO | WO 97/27297 | 7/1997 | |
| WO | WO 97/42949 | 11/1997 | |
| WO | WO 98/56806 | 12/1998 | |
| WO | WO9903508 A2 | 1/1999 | |
| WO | WO 99/06540 | * 2/1999 | ............ C12N 15/00 |
| WO | WO 9906540 | 2/1999 | |
| WO | WO9906540 A3 | 12/1999 | |
| WO | WO 00/52158 | 9/2000 | |

OTHER PUBLICATIONS

Miller 1995, FASEB J., vol. 9, p. 190-199.*
Verma, Sep. 1997, Nature, vol. 389, p. 239-242.*
Crystal, 1995, Science, vol. 270, p. 404-410.*
Ross, Sep. 1996, Human Gene Therapy, vol. 7, p. 1781-1790.*
Janeway, Immunobiology 5th Ed. 2001. Garland Publishing, New York, NY, at p. 502, Figure 13.1.*
Firestein, Arth & Rheum, Nov. 1996; 39(14):1781-1790.*
Tomita (Arthritis & Rheumatism, 1998, vol. 41, Supp. 9, S239, Abstract 1238.*
Ghivizzani (PNAS, 1998, vol. 95, p. 4613-4617).*

Roessler (Human Gene Therapy, Mar. 1995, vol. 6, No. 3, p. 307-316).*
Crystal, Science, vol. 270, pp. 404-410 (1995).
Deonarain, Expert Opinion, Ther. Pat., vol. 8, pp. 58-69 (1998).
Hegen et al., "Utility of animal models for identification of potential therapeutics for rheumatoid arthritis", Ann Rheum Dis., 67:1505-1515 (2008).
Miller, FASEB J., vol. 9, pp. 190-199 (1995).
Ross, Human Gene Therapy, vol. 7(14), pp. 1781-1790 (Sep. 1996).
Tomita et al., Arthritis Rheumatism, vol. 41 (suppl. 9), S239, 1238 (1998).
LaBaer et al, "New functional activities for the p21 family of CDK inhibitors," Genes & Development, vol. 11, pp. 847-862 (1997).
Pap et al., Arthritis Rheumatism, vol. 41, (suppl. 9), S239, 1238 (1998).
Firestein, "Invasive fibroblast-like synoviocytes in rheumatoid arthritis. Passive responders or transformed aggressors?," Arthritis Rheum. 39(11):1781-1790 (1996).
Ghivizzani et al., "Direct gene delivery strategies for the treatment of rheumatoid arthritis", Drug Discovery Today, 6(5):259-267 (2001).
Harper et al., "The P21 Cdk-Interacting Protein Cip1 Is a Potent Inhibitor of G1 Cyclin-Dependent Kinases," Cell, 75:805-816 (1993).
Janeway et al., *Immunobiology*, 5$^{th}$ Ed. 2001. Garland Publishing, New York, NY, at p. 502, figure 13.1.
Nasu et al., "Adenoviral transfer of cyclin-dependent kinase inhibitor genes suppresses collagen-induced arthritis in mice," J. Immunol. 165(12):7246-52 (2000).
Nonomura et al., "Suppression of Arthritis by Forced Expression of Cyclin-Dependent Kinase Inhibitor p21 Cip1 Gene Into the Joints," Arthritis & Rheumatism (Abstract Supplement) 42(9):S107, 1999.

(Continued)

*Primary Examiner* — Michael C. Wilson
(74) *Attorney, Agent, or Firm* — Fish & Richardson P.C.

(57) ABSTRACT

The onset ratios and pathological conditions of collagen-induced arthritis and adjuvant arthritis in model mice and rats, respectively, were successfully ameliorated by topically expressing the cyclin-dependent kinase inhibitors p16$^{INK4a}$ and p21$^{Cip1}$ in articular tissues using adenoviral vectors. In the synovial cells of CDKI-transduced mice, expression of inflammatory cytokines was inhibited. Described are the use of the p21$^{Cip1}$ protein for inhibiting abnormal proliferation of synovial tissues, inflammation in synovial tissues and/or expression of inflammatory cytokines in synovial tissues; the p21$^{Cip1}$ gene; compounds promoting the activity or expression of the p21$^{Cip1}$ protein; and pharmaceutical compositions containing these molecules. Also provided are method of screening for compounds participating in the abnormal proliferation of synovial tissues, inflammation in synovial tissues and/or the expression of inflammatory cytokines in synovial tissues targeting the p21$^{Cip1}$ protein. Rheumatoid arthritis and other disorders associated with inflammation of the synovial tissue can be prevented or treated by promoting expression or function of p21$^{Cip1}$ protein.

15 Claims, 13 Drawing Sheets

(56) References Cited

OTHER PUBLICATIONS

Nonomura et al., "Suppression of Arthritis by Forced Expression of Cyclin-Dependent Kinase Inhibitor p21 Cip1 Gene Into the Joints," International Immunology, 13(6):723-731 (2001).

Pindzola et al., "Expression of $p21^{WAF1/CIP1}$ in Soft Tissue Sarcomas: A Comparative Immunohistochemical Study with p53 and Ki-67," Pathology Research and Practice, 194(10):685-691 (1998).

Smith et al., "p21CIP1-mediated inhibition of cell proliferation by overexpression of the gax homeodomain gene," Genes Dev. 11(13):1674-89 (1997).

Sugiyama et al., "Localisation of apoptosis and expression of apoptosis related proteins in the synovium of patients with rheumatoid arthritis," Ann. Rheum. Dis. 55(7):442-449 (1996).

Taniguchi et al., "Induction of the p16INK4a senescence gene as a new therapeutic strategy for the treatment of rheumatoid arthritis," Nat. Med. 5(7):760-7 (1999).

Terada et al., "Overexpression of cell cycle inhibitors (p16INK4 and p21Cip1) and cyclin D1 using adenovirus vectors regulates proliferation of rat mesangial cells," J. Am. Soc. Nephrol. 8(1):51-60 (1997).

Verma and Somia, "Gene therapy—promises, problems and prospects," Nature, 389(6648):239-242. (1997).

Restriction Requirement in U.S. Appl. No. 10/088,661, mailed Feb. 14, 2006 (5 pages).

Fish & Richardson P.C., Response to Restriction Requirement in U.S. Appl. No. 10/088,661, mailed Feb. 14, 2006, filed Aug. 4, 2006 (3 pages).

Office Action in U.S. Appl. No. 10/088,661, mailed Nov. 2, 2006 (17 pages).

Restriction Requirement in U.S. Appl. No. 11/799,353, mailed Apr. 6, 2009 (6 pages).

Fish & Richardson P.C., Response to Restriction Requirement in U.S. Appl. No. 11/799,353, filed May 4, 2009 (2 pages).

Office Action in U.S. Appl. No. 11/799,353, mailed Aug. 20, 2009 (15 pages).

Fish & Richardson P.C., Response to Office Action in U.S. Appl. No. 11/799,353, filed Jan. 19, 2010 (47 pages).

Notice of Allowance in U.S. Appl. No. 11/799,353, mailed Mar. 1, 2010 (6 pages).

Fish & Richardson P.C., Response to Notice of Allowance in U.S. Appl. No. 11/799,353, Issue Fee Transmittal Part B and Comments on Examiner's Reasons for Allowance, filed May 28, 2010, (4 pages).

Fish & Richardson P.C., Response to Office Action in U.S. Appl. No. 11/799,353, mailed Apr. 28, 2011, filed Oct. 26, 2011 (10 pages).

Gene Transfer and Therapy Clinical Trials—update, The Journal of Gene Medicine, vol. 1, pp. 71-73 (1999).

Celebrex (celecoxib capsules) prescribing information, Distributed by G.D. Searle LLC, 25 pages, Jul. 2005.

Final Office Action in U.S. Appl. No. 11/799,353, mailed Apr. 28, 2011 (11 pages).

Tereda et al., "Cell cycle inhibitors ($p24^{Kip1}$ and $p21^{CIP1}$) cause hypertrophy in LLC-PK1 cells," Kidney International, vol. 56, pp. 494-501 (1999).

Deonarain, "Ligand-targeted receptor-mediated vectors for gene delivery," *Expert Opin. Ther. Pat.* 8:53-69, 1998.

Eastham et al., "In Vivo Gene Therapy with p53 or p21 Adenovirus for Prostate Cancer," *Cancer Research* 55:5151-5155, 1995.

Hegen et al., "Utility of Animal Models for Identification of Potential Therapeutics for Rheumatoid Arthritis," *Ann Rheum Dis.* 67:1505-1515, 2008.

Office Action in U.S. Appl. No. 11/799,353, mailed Nov. 8, 2011 (21 pages).

Fish & Richardson P.C., Response to Office Action in U.S. Appl. No. 11/799,353, mailed Nov. 8, 2011, filed May 7, 2012 (21 pages).

Firestein et al., "Apoptosis in Rheumatoid Arthritis Synovium," *J. Clin. Invest.* 96:1631-1638 (1995).

Fish & Richardson P.C., Petition to Withdraw from Issue and Request for Continued Examination in U.S. Appl. No. 11/799,353, filed Jul. 7, 2010, 2 pages.

Office Action in U.S. Appl. No. 11/799,353, mailed Aug. 4, 2010, 10 pages.

Fish & Richardson P.C., Response to Office Action of Aug. 4, 2010 in U.S. Appl. No. 11/799,353, filed Feb. 3, 2011, 12 pages.

Fish & Richardson P.C., Response to Office Action of Jul. 12, 2012 in U.S. Appl. No. 11/799,353, filed Jan. 11, 2013, 19 pages.

Office Action in U.S. Appl. No. 11/799,353, mailed Apr. 8, 2013, 16 pages.

\* cited by examiner

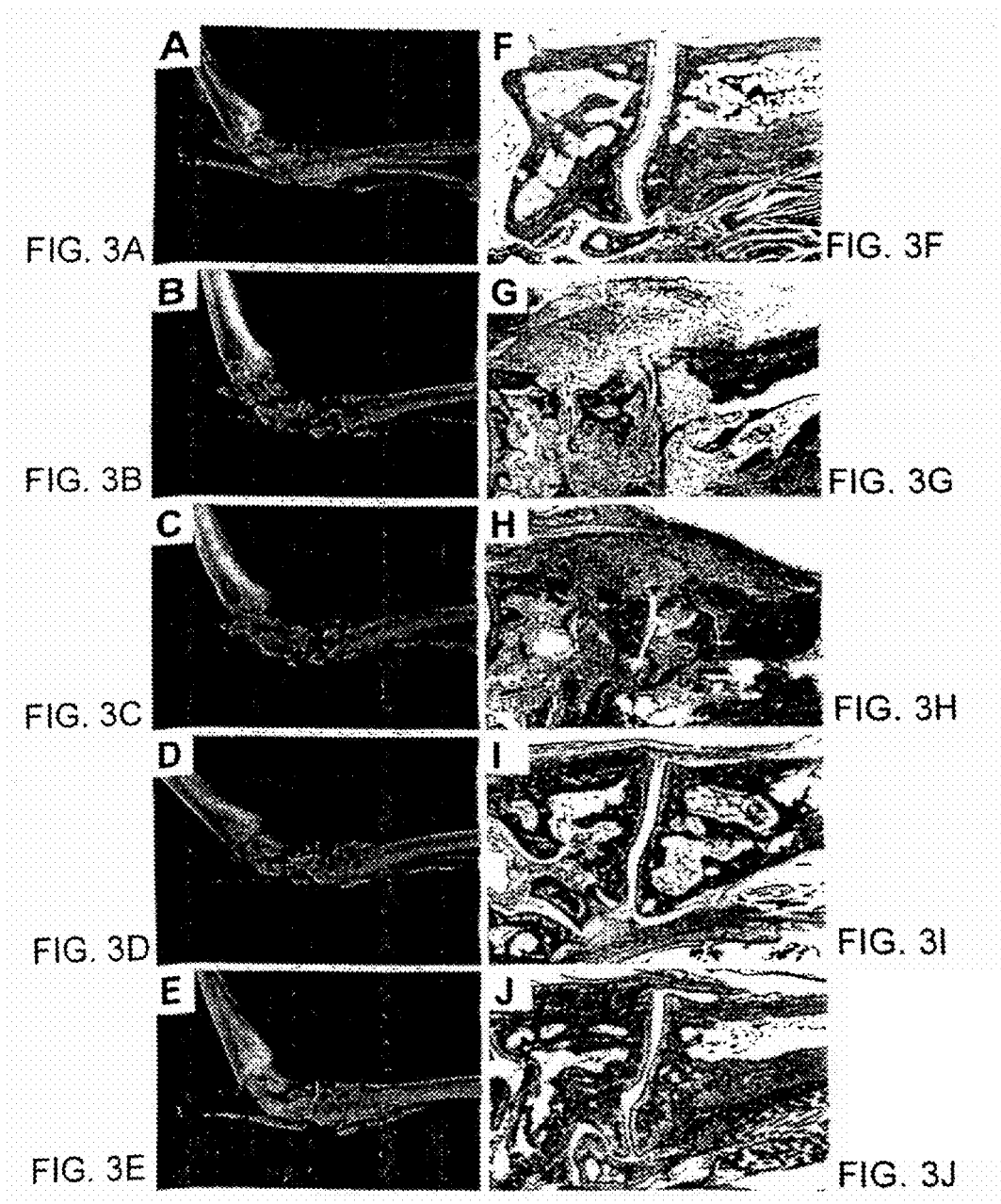

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 1
aacgcaccga atagttacgg                                          20

<210> SEQ ID NO 2
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 2
gcatggttac tgcctctggt                                          20

<210> SEQ ID NO 3
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 3
actgtgatgc gctaatggc                                           19

<210> SEQ ID NO 4
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 4
atggtcttcc tctgctgtcc                                          20

<210> SEQ ID NO 5
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 5
acttaatcgc cttgcagcac                                          20

<210> SEQ ID NO 6
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 6
catctgaact tcagcctcca                                          20

<210> SEQ ID NO 7
<211> LENGTH: 18
<212> TYPE: DNA

```
<213> ORGANISM: Artificial Sequence
<220> FEATURE:
<223> OTHER INFORMATION: Artificially synthesized primer sequence

<400> SEQUENCE: 7
ctgaaagctc tccacctc                                                   18

<210> SEQ ID NO 8
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 8
ggtgctgatg taccagttgg                                                 20

<210> SEQ ID NO 9
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 9
gagacttcca tccagttgcc                                                 20

<210> SEQ ID NO 10
<211> LENGTH: 19
<212> TYPE: DNA
<213> ORGANISM: Artificial Sequence
<220> FEATURE:
<223> OTHER INFORMATION: Artificially synthesized primer sequence

<400> SEQUENCE: 10
ttctgcaagt gcatcatcg                                                  19

<210> SEQ ID NO 11
<211> LENGTH: 17
<212> TYPE: DNA
<213> ORGANISM: Artificial Sequence
<220> FEATURE:
<223> OTHER INFORMATION: Artificially synthesized primer sequence

<400> SEQUENCE: 11
gccaccacgc tcttctg                                                    17

<210> SEQ ID NO 12
<211> LENGTH: 17
<212> TYPE: DNA
<213> ORGANISM: Artificial Sequence
<220> FEATURE:
<223> OTHER INFORMATION: Artificially synthesized primer sequence

<400> SEQUENCE: 12
atgggctcat accaggg                                                    17

<210> SEQ ID NO 13
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 13
aagaaggtgg tgaagcaggc                                                 20
```

```
<210> SEQ ID NO 14
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 14
tccaccaccc tgttgctgta                                              20
```

METHODS OF TREATMENT USING A VECTOR ENCODING P21/$^{Cip1}$

CLAIM OF PRIORITY

This application is a continuation of U.S. patent application Ser. No. 11/799,353, filed May 1, 2007, now abandoned, which is a continuation of U.S. patent application Ser. No. 10/088,661, filed on Jul. 19, 2002, now abandoned, which is the U.S. National Phase of International Patent Application No. PCT/JP00/06511, filed on Sep. 22, 2000, which claims the benefit of Japanese Patent Application No. 11-269579, filed on Sep. 22, 1999. The entire contents of each of the foregoing applications are hereby incorporated by reference.

TECHNICAL FIELD

The present invention relates to molecules for suppressing inflammation of Rheumatoid arthritis (RA) and the screening of those molecules.

BACKGROUND ART

Rheumatoid arthritis (RA) is characterized by the synovial inflammation of multiple joints. The affected synovial tissues contain activated macrophages, fibroblasts, T- and B-lymphocytes. The synovial fibroblasts proliferate and release tissue-degrading enzymes in response to pro-inflammatory cytokines, such as interleukin (IL)-1β, tumor necrosis factor (TNF)-α, and IL-6, which are produced in situ (Arend, W. P. and J. M. Dayer, 1995, Arthritis Rheum. 38: 151-160; Feldmann, M. et al., 1996, Cell 85: 307-310). The resulting hyperplastic synovial membrane, termed pannus, irreversibly destroys the cartilage and bone of the affected joints.

Almost all of the conventional anti-rheumatic drugs and recently developed biological reagents are aimed primarily at the suppression of inflammatory mediators involved in RA. Most of the biological reagents are intended to neutralize pro-inflammatory cytokines, such as TNF-α, IL-1, or IL-6 (Elliott, M. J. et al., 1994, Lancet. 344:1105-1110; Moreland, L. W. et al., 1997, N. Engl. J. Med. 337: 141-147; Campion, G. V. et al., 1996, Arthritis Rheum. 39: 1092-1101; Arend, W. P. et al., 1998, Annu. Rev. Immunol. 16: 27-55; Yoshizaki, K. et al., 1998, Springer Semin. Immunopathol. 20: 247-259). Hydroxychloroquine, d-penicillamine, gold, sulfasalazine, immunosuppressive methotrexate, and such, are included as representative anti-rheumatic drugs. Although, target molecules responsible for their anti-rheumatic effects are not accurately known, they are considered to suppress the inflammatory processes (Conaghan, P. G. et al., 1997, Curr. Opinion Rheumatol. 9: 183-190). In contrast, newly developed drugs, such as leflunomide, cyclosporin A, and FK506 inhibit intracellular molecules essential for the activation of the immunocompetent cells involved in the rheumatoid synovitis. The TNF-α antagonists (such as remicade and infliximab) neutralize the inflammatory mediators released by the synovial cells. Most patients respond well to these drugs, but some are resistant or the effect of these drugs decreases after a period of disease remission in other patients. Moreover, there is little evidence proving that these drugs arrest the progression of the disease in the long run. It is presumed that the suppression of one inflammatory mediator might activate other mediators because of the complexity and redundancy of the inflammatory pathways. Therefore, it is believed that the total prevention of joint destruction is not available through conventional treatments. In contrast to this, the present inventors have investigated means for preventing the creation of the destructive synovium hyperplasia by directly inhibiting the growth of the synovial fibroblast itself using cell-cycle-suppressing proteins called cyclin-dependent kinase inhibitors (CDKIs).

The CDKI molecules consist of the INK4 family and the Cip/Kip family, each of which comprise three to four members, respectively (Sherr, C. J. and J. M. Roberts., 1995, Genes Dev. 9: 1149-1163). The expression of individual CDKIs is regulated independently, suggesting that each CDKI plays a unique role in the control of the cell cycle. p16$^{INK4a}$, belonging to the INK4 family, binds to cyclin D and prevents the formation of catalytically active kinase complexes with the cyclin-dependent kinase (CDK) 4 or CDK6. Accordingly, p16$^{INK4a}$ inhibits the cell cycle at the G$_1$/S transition (Lukas, J. et al., 1995, Nature 375: 503-506; Koh, J. et al., 1995, Nature 375: 506-510; Serrano, M., 1997, Exp. Cell Res. 237: 7-13). p21$^{Cip1}$, which belongs to the Cip/Kip family, inhibits a wide variety of cyclin/CDK complexes (Harper, J. W. et al., 1993, Cell 75: 805-816; Xiong, Y. et al., 1993, Nature 366: 701-704). p21$^{Cip1}$ also binds to the proliferating cell nuclear antigen (PCNA), which activates DNA polymerase δ and inactivates PCNA (Flores-Rozas, H. et al., 1994, Proc. Natl. Acad. Sci. USA. 91: 8655-8659; Nakanishi, M. et al., 1995, J. Biol. Chem. 270: 17060-17063; Waga, S. et al., 1994, Nature 369: 574-578; Li, R. et al., 1994, Nature 371: 534-537). As described above, p21$^{Cip1}$ inactivates the kinase activity of cyclin/CDK complexes at various stages of cell cycle and simultaneously inhibits DNA replication.

The present inventors have previously studied the expression of CDKIs in rheumatoid synovial tissues (Taniguchi, K. et al., 1999, Nature Med. 5: 760-767). CDKI belong to a group of intranuclear molecules. The inventors found that rheumatoid synovial fibroblasts (RSFs) derived from rheumatoid synovial tissues do not express CDKI p16$^{INK4a}$ in vivo, but readily express them when their growth is inhibited in vitro. Specific induction of p16$^{INK4a}$ in RSFs derived from RA patients was observed. Therefore, the inventors conducted experiments wherein the p16$^{INK4a}$ gene was transfected by means of an adenovirus into the joints of rats with adjuvant arthritis (AA). This administration successfully suppressed the synovial hyperplasia and other associated pathology of arthritis (Taniguchi, K. et al., 1999, Nature Med. 5: 760-767). The arthritis treatment by p16$^{INK4a}$ induction compares well with conventional anti-rheumatic drugs and recently developed biological reagents.

On the other hand, p21$^{Cip1}$ is a CDKI belonging to a different family than that of p16$^{INK4a}$. p21$^{CiP1}$, as well as p16$^{INK4a}$, are not expressed in vivo in fibroblasts derived from synovial tissue of rheumatism, but their expression is induced in vitro when the growth of fibroblasts is inhibited. However, unlike p16$^{INK4a}$, the induction of p21$^{Cip1}$ is also observed in fibroblasts of nonrheumatoid origin (Taniguchi, K. et al., 1999, Nature Med. 5: 760-767). Additionally, in comparison to p16$^{INK4a}$, p21$^{Cip1}$ inhibits all kinds of CDKs. Forced expression of p21$^{Cip1}$ also arrests cell cycle of normal and tumor cells at the G1 phase (Dimri, G. P. et al., 1996, Mol. Cell. Biol. 16: 2987-2997). The p16$^{INK4a}$ protein level gradually rises and stays high in the senescent cells. In contrast, the expression level of p21$^{Cip1}$ in fibroblasts goes up with an increase in cell division, and decreases when the cells approach senescence (Tahara, H. et al., 1995, Oncogene 10: 835-840). Although p16$^{INK4a}$ gene expression appears to have a more direct impact in senescence induction (Alcorta, D. A. et al., 1996, Proc. Natl. Acad. Sci. USA 93: 13742-13747), the biological function of p21$^{Cip1}$ is more complex. In certain settings, p21$^{Cip1}$ promotes the formation of active kinase complexes by cyclin and CDK, and promotes the cell cycle rather than stopping it (LaBaer, J. et al., 1997, Genes Dev. 11: 847-862). Whereas the N-terminal domain of p21$^{Cip1}$ interacts with CDK/cyclin complexes, the C-terminal domain binds to and inhibits the proliferation cell nuclear antigen (PCNA), a subunit of DNA polymerase δ essential for DNA replication and repair (Li, R. et al., 1994, Nature 371: 534-537). Furthermore, the expression of p21$^{Cip1}$ enhances NF-κB-dependent gene expression by inhibiting cyclin E/CDK2, which binds to the complexes of p300/CBP coactivators and NF-κB (Perkins, N. D. et al., 1997, Science 275: 523-527). In addition, the forced expression of p21$^{Cip1}$ in certain cell lines was shown to induce apoptotic cell death (Tsao, Y. P. et al., 1999, J. Virol. 73: 4983-4990; Matsushita, H. et al., 1998, Hypertension 31: 493-498; Kondo, Y. et al., 1997, Exp. Cell Res. 236: 51-56; Sheikh, M. S. et al., 1995, Oncogene 11: 1899-1905). Moreover, biological effects, other than inhibition of kinase activity, are distinct between p16$^{INK4a}$ and p21$^{Cip1}$ (LaBaer, J. et al., 1997, Genes Dev. 11: 847-862; Li, R. et al., 1994, Nature 371: 534-537; Xiong, Y. et al., 1993, Nature 366: 701-704). Disruption of the p16$^{INK4a}$ gene, which results in frequent tumor development in a murine model, is also different from the result obtained by p21$^{Cip1}$ gene disruption (Serrano, M. et al., 1996, Cell 85: 27-37). Thus, it was not known if p21$^{Cip1}$, which is distinguished structurally from p16$^{INK4a}$ and also differs in its mode of expression and inhibition of cell cycle, had a therapeutic effect on rheumatoid arthritis.

DISCLOSURE OF THE INVENTION

The present invention is based on the finding that an anti-inflammatory effect can be obtained by raising the expression of p21$^{Cip1}$ protein in inflammation synovial tissue. The objective of the present invention is to inhibit aberrant growth and/or inflammation of the synovial tissue by promoting expression or function of p21$^{Cip1}$ protein. More specifically, the present invention provides p21$^{Cip1}$ protein and p21$^{Cip1}$ gene for inhibiting the aberrant growth, inflammation and/or the expression of inflammatory cytokine of synovial tissue, the use of compounds which increase the activity or the amount of p21$^{Cip1}$ protein, and pharmaceutical compositions comprising these molecules. Moreover, the present invention provides methods of screening for compounds which increase the activity or the amount of p21$^{Cip1}$ protein.

The present inventors conducted experiments examining the therapeutic effects that arise when the expression of p16$^{INK4a}$ or p21$^{Cip1}$ gene is forced in mouse inflammatory synovial tissue, by using mouse collagen-induced arthritis (CIA), an animal model of rheumatoid arthritis (RA). Like adjuvant arthritis (AA) in rats, this model demonstrates remarkable similarities to human RA (Courtenay, J. S. et al., 1980, Nature 283: 666-668; Wooley, P. H. et al., 1981, J. Exp. Med. 154: 688-700; Holmdahl, R. et al., 1988, Lab. Invest. 58: 53-60). As a result, the present inventors found that not only the gene transfection of p16$^{INK4a}$, but also that of p21$^{Cip1}$, exerts anti-arthritic effects. Pannus formation, which results from the proliferation of synovial fibroblasts, was significantly suppressed by the gene transfection. No destruction of the cartilage or bone was seen. Moreover, the infiltration of mononuclear cells into the synovial tissues was also suppressed. The anti-arthritic effects were obvious even after the crisis of arthritis.

The present inventors speculated that the induction of p21$^{Cip1}$ or p16$^{INK4a}$ not only makes synovial cells refractory to proliferative stimuli but also may exert some anti-inflammatory effects. To confirm the hypothesis, the expression of inflammatory cytokines in the CIA joints was examined. As in RA, joint inflammation and cartilage destruction depend on IL-1 and TNF-α in the affected joints in CIA. Administration of monoclonal antibodies (mAb) against either of the cytokines ameliorated the arthritis (Piguet, P. F. et al., 1992, Immunology 77: 510-514; Williams, R. O. et al., 1992, Proc. Natl. Acad. Sci. USA. 89: 9784-9788; Geiger, T. et al., 1993, Clin. Exp. Rheumatol. 11: 515-522; Van den Berg, W. B. et al., 1994, Clin. Exp. Immunol. 95: 237-243; Thorbecke, G. J. et al., 1992, Proc. Natl. Acad. Sci. USA. 89: 7375-7379). Indeed, the RT-PCR and immunohistochemical analyses revealed that expression of these cytokines was significantly suppressed when the p21$^{Cip1}$ or p16$^{INK4a}$ gene was transfected into the joints.

In vitro experiments using RSF revealed that the forced expression of the p21$^{Cip1}$ gene inhibited growth of transfected cell without inducing their apoptotic cell death. The present inventors further assessed the effects of p21$^{Cip1}$ gene therapy using the rat AA model. As observed in the CIA model, significant therapeutic effects were observed in AA rat by intraarticular p21$^{Cip1}$ gene transfection therapy. These in vivo and in vitro effects were comparable to those of the p16$^{INK4a}$ gene transfection. Gene transfection significantly inhibited synovial thickening, mononuclear cell infiltration, pannus formation, and cartilage degeneration in affected synovial tissues. The effect of p21$^{Cip1}$ gene therapy was obvious clinically as well as histologically. Reduced frequency of the PCNA-expressing cells in synovial tissues of the p21$^{Cip1}$-treated joints showed that p21$^{Cip1}$ gene therapy indeed inhibited cell growth in vivo.

From these results, the present inventors discovered that the induction of CDKI gene expression in rheumatic synovial tissue, especially the induction of p21$^{Cip1}$, may be an effective strategy for the treatment of RA, and that the ectopic expression of CDKI not only prevents overgrowth of synovium but also mitigates inflammation induction environment in morbid joint. Moreover, these findings suggest that synthetic compounds and such which selectively promote expression of p16$^{INK4a}$ or p21$^{CIP1}$ also function as a therapeutic reagent toward RA. Such compounds, which can regulate aberrant growth of synovial cells or inflammation of synovium, can be efficiently screened by targeting the p21$^{Cip1}$ protein. Moreover, application toward the prevention or the therapy of diseases caused from aberrant growth and/or inflammation of synovial cells, such as RA, is expected for the p21$^{Cip1}$ protein, the p21$^{Cip1}$ gene, and compounds obtained by such screening.

The present invention is based on findings described above, and more specifically provides the following:

(1) a cyclin-dependent kinase inhibitor p21$^{Cip1}$ protein, which is used for the inhibition of aberrant growth of synovial tissue, inflammation of synovial tissue, and/or the expression of inflammatory cytokines in synovial tissue;

(2) a DNA encoding cyclin-dependent kinase inhibitor p21$^{Cip1}$ protein, which is used for the inhibition of aberrant growth of synovial tissue, inflammation of synovial tissue, and/or the expression of inflammatory cytokines in synovial tissue;

(3) a compound used for the inhibition of aberrant growth of synovial tissue, inflammation of synovial tissue, and/or the expression of inflammatory cytokines in synovial tissue selected from the group of:
  (a) a compound which promotes the activity of cyclin-dependent kinase inhibitor p21$^{Cip1}$,
  (b) a compound which inhibits the degradation of cyclin-dependent kinase inhibitor p21$^{Cip1}$ protein, and
  (c) a compound which promotes the expression of endogenous cyclin-dependent kinase inhibitor p21$^{Cip1}$ gene;

(4) a pharmaceutical composition for the prevention or the treatment of rheumatoid arthritis comprise as the active ingredient the protein described in (1), the DNA described in (2), or the compounds described in (3);

(5) a method of screening for compounds that inhibit aberrant growth of synovial tissue, inflammation of synovial tissue, and/or the expression of inflammatory cytokines in synovial tissue, comprising the steps of:
   (a) contacting the cyclin-dependent kinase inhibitor $p21^{Cip1}$ protein with a test sample,
   (b) detecting inhibition of cyclin-dependent kinase of said $p21^{Cip1}$ protein, and,
   (c) selecting compounds which increase the inhibition in comparison to that occurring in the absence of test compound;

(6) a method of screening for compounds that inhibit aberrant growth of synovial tissue, inflammation of synovial tissue, and/or the expression of inflammatory cytokines in synovial tissue, comprising the steps of:
   (a) contacting the cyclin-dependent kinase inhibitor $p21^{Cip1}$ protein with a test sample,
   (b) detecting the amount of said $p21^{Cip1}$ protein, and,
   (c) selecting compounds which increase the amount of said $p21^{Cip1}$ protein, in comparison to that occurring in the absence of the test compound;

(7) a method of screening for compounds that inhibit aberrant growth of synovial tissue, inflammation of synovial tissue, and/or the expression of inflammatory cytokines in synovial tissue, comprising the steps of:
   (a) contacting cells expressing the intrinsic cyclin-dependent kinase inhibitor $p21^{Cip1}$ gene with a test sample,
   (b) detecting the amount of transcriptional product of said $p21^{Cip1}$ gene, and,
   (c) selecting compounds which increase the amount of transcriptional product of said $p21^{Cip1}$ gene, in comparison to that occurring in the absence of the test compound;

(8) a method of screening for compounds that inhibit aberrant growth of synovial tissue, inflammation of synovial tissue, and/or the expression of inflammatory cytokines in synovial tissue, comprising the steps of:
   (a) contacting cells containing a vector, in which a reporter gene is functionally ligated downstream of an expressional regulation domain of an intrinsic cyclin-dependent kinase inhibitor $p21^{Cip1}$ gene, with a test sample,
   (b) detecting the reporter activity, and,
   (c) selecting compounds which increase the reporter activity in comparison to that occurring in the absence of the test compound.

The present invention provides $p21^{Cip1}$ protein, which is used for the inhibition of aberrant growth of synovial tissue, inflammation of synovial tissue, and/or the expression of inflammatory cytokines in synovial tissue, and DNA encoding said protein. The phrase "use for the inhibition of aberrant growth of synovial tissue, inflammation of synovial tissue, and/or the expression of inflammatory cytokines in synovial tissue" herein, includes the use as an reagent for the inhibition of aberrant growth of synovial tissue (or cells), inflammation of synovial tissue, and/or the expression of inflammatory cytokines in synovial tissue; and the use as a drug for the inhibition of aberrant growth of synovial tissue, inflammation of synovial tissue, and/or the expression of inflammatory cytokines in synovial tissue in patients. For example, IL-1β, TNFα, and IL-6 can be exemplified as inflammatory cytokines. Moreover, herein, the phrase "use for the inhibition of aberrant growth of synovial tissue, inflammation of synovial tissue, and/or the expression of inflammatory cytokines in synovial tissue" also includes the use for the mitigation of symptom of disease caused by aberrant growth of synovial tissue, inflammation of synovial tissue, and/or the expression of inflammatory cytokines in synovial tissue, including hyperplasia of synovium, pannus formation and infestation, infiltration of immunocytes such as monocyte through joint tissue, and destruction of cartilage or bone in joint.

The $p21^{Cip1}$ protein used for the inhibition of aberrant growth of synovial tissue, inflammation of synovial tissue, and/or the expression of inflammatory cytokines in synovial tissue in the present invention may be either of natural protein or recombinant protein made by gene recombination technology. These proteins can be prepared by well-known protein purification techniques or genetic engineering methods. More specifically, the natural protein can be prepared, for example, by isolating the $p21^{Cip1}$ protein from tissues or cells that show a high level of expression of the protein, such as HeLa cell or fibroblasts cultured successively, by affinity chromatography using antibodies against partial peptides of the $p21^{Cip1}$ protein. On the other hand, a recombinant protein can be prepared, for example, by culturing cells transfected with DNA encoding the $p21^{Cip1}$ protein (Harper, J. W. et al., 1993, Cell 75, 805-816; El-Deiry, W. S. et al., 1993, Cell 75, 817-825 (GenBank Ac. No. U03106); Noda, A. et al., 1994, Exp. Cell Res. 211, 90-98), and recovering the protein expressed from the cells or the culture supernatant thereof. Cells used for the production of recombinant proteins include mammalian cells such as, COS cells, CHO cells, and NIH3T3 cells; insect cells such as Sf9 cells; yeast cells; and *E. coli* cells. Vectors for expressing the recombinant proteins within cells vary according to the host used, for example, pcDNA3 (INVITROGEN), pEF-BOS (Nucleic Acids Res. 1990, 18 (17), p5322), and such are used as vectors for mammalian cells; the BAC-TO-BAC baculovirus expression system (GIBCO BRL), and such are used for insect cells; *Pichia* Expression Kit (INVITROGEN), and such are used for yeast cells; pGEX-5x-1 (Pharmacia), QIAEXPRESS expression system (QIAGEN), and such are used for *E. coli* cells. Vectors are transfected to hosts using, for example, the calcium phosphate method; the DEAE dextran method; methods using cationic liposome DOTAP (BOEHRINGER MANNHEIM), and SUPERFECT (QIAGEN); electroporation method; the calcium chloride method; and such. The recombinant protein can be purified from the obtained transformant according to conventional methods, for example, those described in "The QIAEXPRESSIONIST Handbook," QIAGEN, Hilden, Germany.

One skilled in the art can easily replace, delete, add, and/or insert amino acid (s) in the amino acid sequence of the $p21^{Cip1}$ protein to elevate its activity, stability, and such using well-known methods, such as the site-specific mutagenetic system using PCR (GIBCO-BRL, Gaithersburg, Md.), site-specific mutagenesis using oligonucleotides (Kramer, W. and Fritz, H. J. (1987) Methods in Enzymol., 154: 350-367), the Kunkel method (Methods Enzymol. 85, 2763-2766 (1988)), and so on. Such modified $p21^{Cip1}$ proteins are also included in the present invention.

Either cDNA or genomic DNA can be used as the DNA which encodes the $p21^{Cip1}$ protein used for the inhibition of aberrant growth of synovial tissue, inflammation of synovial tissue, and/or the expression of inflammatory cytokines in synovial tissue. The nucleotide sequences of $p21^{Cip1}$ cDNA and $p21^{Cip1}$ genomic DNA are disclosed in "Harper, J. W. et al., 1993, Cell 75, 805-816; El-Deiry, W. S. et al., 1993, Cell 75, 817-825 (GenBank Accession No. U03106); Noda, A. et al., 1994, Exp. Cell Res. 211, 90-98)".

p21$^{Cip1}$ cDNA and p21$^{Cip1}$ genomic DNA can be prepared by synthesizing oligonucleotides (in general, 15 to 50 bases) based on the disclosed sequence information described above, and then amplifying by carrying out polymerase chain reaction using said oligonucleotides as primers and cDNA originated from tissue or cells expressing p21$^{Cip1}$ as the template. Moreover, p21$^{Cip1}$ cDNA and p21$^{Cip1}$ genomic DNA can also be prepared by screening cDNA libraries or genomic libraries by the plaque hybridization method or the colony hybridization method, using DNA fragments comprising a portion of the disclosed sequence described above as a primer. For example, a cDNA library derived from human HeLa cells can be used. Moreover, commercially available cDNA libraries and genomic libraries (CLONTECH) can be also used. Polymerase chain reaction or hybridization method mentioned above can be conducted by ordinary methods described in experiment books, such as in the literature "Sambrook et al., Molecular Cloning, Cold Spring Harbor Lab. Press". DNA fragments amplified by the polymerase chain reaction and DNA fragments screened by the hybridization can be subcloned into suitable plasmid DNA and such, and may be used for gene expression experiments.

Further, according to the present invention, compounds which promote the activity of the p21$^{Cip1}$ protein (such as cyclin-dependent kinase inhibiting activity, PCNA inhibiting activity, or the like), compounds which inhibit the degradation of the p21$^{Cip1}$ protein, and compounds which promote the expression of the p21$^{Cip1}$ gene can also be used for the inhibition of aberrant growth of synovial tissue, inflammation of synovial tissue, and/or the expression of inflammatory cytokines in synovial tissue. As shown in the Examples, it was found that the topical expression of the p21$^{Cip1}$ proteins in the joint shows anti-arthritic action. Therefore, it is considered that aberrant growth of synovial tissue can be inhibited by enhancing the amount or function of p21$^{Cip1}$ protein in joint, especially in synovial tissue.

For example, p21$^{Cip1}$ expression is immediately, though transiently, induced by the p53 transcription factor in response to a DNA damage (Dulic, V. et al., 1994, Cell. 76: 1013-1023; El-Deiry, W. S. et al., 1994, Cancer Res. 54: 1169-1174). It is also induced in a p53-independent fashion under a variety of growth-inhibitory conditions, such as culture at high density or in low-serum media. The p21$^{Cip1}$ gene is also induced by serum, growth factors, and IL-6 in some cell lines (Gartel, A. L. and Tyner, A. L., 1999, Exp. Cell Res. 246: 280-289; Bellido, T. et al., 1998, J. Biol. Chem. 273: 21137-21144). Many compounds that induce p21$^{Cip1}$ in various human cell lines have already been identified (Barboule, N. et al., 1997, Oncogene 15: 2867-2875; Sheikh, M. S. et al., 1994, Oncogene 9: 3407-3415; Gorospe, M. et al., 1999, Gene Express. 7: 377-385), and include histone deacetylase inhibitors, such as butyrate and Trichostatin A; 12-O-tradecanoylphorbol-13-acetate; cholecalciferol; retinoic acid; mimosine; and okadaic acid (Nakano, K. et al., 1997, J. Biol. Chem., 272, 22199-22206; Sowa, Y. et al., 1997, Biochem. Biophys. Res. Commun., 241, 142-150; Alpan, R. S, and A. B. Pardee., 1996, Cell Growth Different. 7: 893-901; Jiang, H. et al., 1994, Oncogene 9: 3397-3406; Steinman, R. A. et al., 1994, Oncogene 9: 3389-3396). Thus, these compounds which promote expression of the cellular p21$^{Cip1}$ gene can be preferably used in the present invention. In addition, the induction of p21$^{Cip1}$ may compensate for the abnormal expression of p53 in rheumatoid synovial tissues reported by Firestein and his colleagues (Firestein, G. S. et al., 1997, Proc. Natl. Acad. Sci. USA. 94: 10895-10900; Tak, P. P. et al., 1999, Arthritis Rheum. 42: 948-953).

p21$^{Cip1}$ protein is contacted to test compounds and compounds which increase its cyclin dependent kinase inhibiting activity are selected in the preparation of compounds which promote cyclin dependent kinase inhibiting activity of p21$^{Cip1}$ protein. More specifically, compounds which promote the cyclin dependent kinase inhibiting activity of p21$^{Cip1}$ protein can be screened by a method comprising the steps of: (a) contacting the p21$^{Cip1}$ protein with a test sample; (b) detecting the cyclin dependent kinase inhibiting activity of the p21$^{Cip1}$ protein; and (c) selecting compounds which increase said activity of the p21$^{Cip1}$ protein in comparison to that occurring in the absence of the test sample.

There is no limitation on the test sample to be used and it may include, for example, cell extracts, cell culture supernatant, products of fermenting microorganism, extracts from marine organism, plant extracts, purified or crude proteins, peptides, non-peptide compounds, synthetic micromolecular compounds and natural compounds. The p21$^{Cip1}$ protein to be contacted with the test sample can be, for example, a purified protein or in a form bound to a carrier. Alternatively, cells expressing p21$^{Cip1}$ protein can be contacted with the test sample.

The cyclin dependent kinase inhibiting activity of the p21$^{Cip1}$ protein can be detected by measuring, for example, histone phosphorylation activity of cyclin/CDK (Matsushime, H. et al., 1994, Mol. Cell. Biol., 14, 2066-2076).

For preparing compounds which inhibit the degradation of the p21$^{Cip1}$ protein, compounds which suppress the decrease of the amount of p21$^{Cip1}$ protein can be selected by detecting the amount of p21$^{Cip1}$ protein after contacting with a test compound. More specifically, compounds which inhibit the degradation of the p21$^{Cip1}$ protein can be screened by a method comprising the steps of: (a) contacting the p21$^{Cip1}$ protein with a test sample; (b) detecting the amount of the p21$^{Cip1}$ protein; and (c) selecting compounds which increase the amount of the p21$^{Cip1}$ protein in comparison to that occurring in the absence of the test sample.

Test samples are not limited especially as those for the screening methods described above. The protein of the present invention to be contacted with the test samples may be, for example, purified protein or in the form bound to a carrier. Moreover, cells expressing p21$^{Cip1}$ protein may be contacted with the test samples. The detection of the amount of the p21$^{Cip1}$ protein can be conducted with, for example, western blotting method. More specifically, for example, cells expressing the p21$^{Cip1}$ protein are first contacted with a test sample, and then are lysed to subject the lysate to SDS-PAGE. After SDS-PAGE, proteins electrophoresed in the gel are transfected to nitrocellulose membrane or the like. The membrane is contacted with antibodies against the p21$^{Cip1}$ protein, and then, are contacted with labeled secondary antibodies to detect the amount of the p21$^{Cip1}$ protein existing on the membrane. Compounds which increase the amount of the p21$^{Cip1}$ protein can be selected in comparison to that occurring in the absence of the test sample as a control.

To prepare compounds which promote the expression of the p21$^{Cip1}$ gene, compounds that increase the expression of intrinsic p21$^{Cip1}$ gene can be selected after contacting cells expressing said gene with the test sample. More specifically, compounds which promote the expression of the p21$^{Cip1}$ gene can be screened by a method comprising the steps of: (a) contacting cells which express the p21$^{Cip1}$ gene with a test sample; (b) detecting the amount of the p21$^{Cip1}$ gene transcript; and (c) selecting compounds which increase the amount of the p21$^{Cip1}$ gene transcript in comparison to that occurring in the absence of the test sample.

Test samples are not limited specifically as those for the screening methods described above. Moreover, for example, cells such as fibroblast of synovial tissue origin and the like can be suitably used as cells expressing intrinsic $p21^{Cip1}$ gene, but are not limited thereto. The detection of the amount of the $p21^{Cip1}$ gene transcript can be conducted by northern blotting method, RT-PCR method, and such which are well known to one skilled in the art.

Furthermore, compounds which promote the expression of the $p21^{Cip1}$ gene can be screened by a method in which the activation of expressional regulation domain of the $p21^{Cip1}$ gene is used as an index. Additionally, reporter genes can be used for efficient screening. More specifically, the screening can be conducted by a method comprising the steps of: (a) contacting cells which comprise a vector in which a reporter gene is functionally bound downstream of the expressional regulation domain of the $p21^{Cip1}$ gene are contacted with a test sample; (b) detecting the reporter activity; and (c) selecting compounds which increase the reporter activity in comparison to that occurring in the absence of the test sample.

According to the screening method of the present invention, a vector comprising a reporter gene functionally linked downstream of the expression-controlling region of the $p21^{Cip1}$ gene is constructed. Herein, the term "functionally linked" refers to a condition that the expression-controlling region and the reporter gene are linked in such a way that the reporter gene linked downstream of the expression-controlling region can be expressed in response to the activation of the expression-controlling region. For example, firefly luciferase gene, secretory alkaline phosphatase gene, chloramphenicol acetyltransferase (CAT) gene, and such can be used as the reporter gene.

Then, the constructed vector is transfected into mammalian cells, and said cells are contacted with a test sample to detect the reporter activity. Test samples are not limited specifically to those for the screening methods described above. The detection of the reporter activity can be conducted by well known method according to the type of the reporter gene. As a result, compounds which promote the expression of the $p21^{Cip1}$ gene and inhibit aberrant growth of synovial tissue, inflammation of synovial tissue, and/or the expression of inflammatory cytokines in synovial tissue can be screened by selecting compounds which increase reporter activity as compared to the reporter activity in the cells that were not contacted with the test sample. The screening method has a feature that it is simple as compared to the screening using direct detection method, such as northern blotting method or RT-PCR analysis described above, since the expression of $p21^{Cip1}$ gene is detected using a reporter activity as an index.

The expression-controlling region (promoter) of the $p21^{Cip1}$ gene is described in "El-Deiry, W. S. et al., 1995, Cancer Res., 55 (13), 2910-2919 (GenBank Ac. No. U24170); Evans, S. C. et al. (GenBank Ac. No. U50603)". The experiments of transcription control using the expression-controlling region is described in "Nakano, K. et al., 1997, J. Biol. Chem., 272, 22199-22206; Sowa, Y. et al., 1997, Biochem. Biophys. Res. Commun., 241, 142-150".

The $p21^{Cip1}$ protein, DNA which encode said protein, and compounds isolated by the screening described above can be used as reagents for the inhibition of aberrant growth of synovial tissue, inflammation of synovial tissue, and/or the expression of inflammatory cytokines in synovial tissue; or as a pharmaceutical composition for the prevention or treatment of diseases in which aberrant growth or inflammation of synovial tissue (especially, rheumatoid arthritis). is involved. Besides rheumatoid arthritis, for example, juvenile rheumatoid arthritis, other rheumatic diseases with articular inflammation, and osteoarthrosis can be considered as diseases related to aberrant growth and/or inflammation of synovial tissue.

For the use of the $p21^{Cip1}$ protein as a reagent for the inhibition of aberrant growth of synovial tissue, inflammation of synovial tissue, and/or the expression of inflammatory cytokines in synovial tissue, the $p21^{Cip1}$ protein can be introduced into synovial cells by methods, for example, microinjection, and so on.

To use the DNA encoding the $p21^{Cip1}$ protein as a reagent for the inhibition of aberrant growth of synovial tissue, inflammation of synovial tissue, and/or the express ion of inflammatory cytokines in synovial tissue, said DNA can be inserted into a vector, in which the expression of said DNA in synovial cells is assured, and said vector can be transfected into synovial cells. The vector can be transfected into synovial cells by methods known to one skilled in the art, for example, such as direct injection method, calcium phosphate method, DEAE dextran method, cationic liposome method, electroporation method, and lipofection method. Viral vectors such as retrovirus vector, adenovirus vector, and Sendai virus vector can be also used for the transduction.

Where the compounds isolated by the screening described above are used as reagents for the inhibition of aberrant growth of synovial tissue, inflammation of synovial tissue, and/or the expression of inflammatory cytokines in synovial tissue, they may be introduced into synovial cells according to the form of said compounds by methods, for example, such as microinjection method (in the case of high molecular weight compounds such as protein), the gene transfection method such as the calcium phosphate method (in the case where the compound is a gene), the addition into culture media of synovial cells, and so on. The compounds may be administered to synovial tissue in vivo by intraarticular injection and so on. Genes can be administered by using, for example, well known vector systems.

Moreover, in the case of using the $p21^{Cip1}$ protein or compounds which can be obtained by screening described above as pharmaceutical compositions for the inhibition of aberrant growth of synovial tissue, inflammation of synovial tissue, and/or the expression of inflammatory cytokines in synovial tissue, they may be administered after formulating by well known pharmaceutical method besides directly administering them to patients (for example, topical administration into the joint). For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dosage form required for generally accepted drug implementation. The amount of active ingredients in these preparations makes a suitable dosage within the indicated range acquirable.

Examples of additives that can be mixed to tablets and capsules are: binders such as gelatin, corn starch, tragacanth gum, and arabic gum; excipients such as crystalline cellulose; swelling agents such as corn starch, gelatin and alginic acid; lubricants such as magnesium stearate; sweeteners such as sucrose, lactose, and saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

For example, physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80™ and HCO-50.

Sesame oil and soy-bean oil can be used as a oleaginous liquid and may be used in conjunction with benzyl benzoate or benzyl alcohol as solubilizers and may be formulated with buffer, such as phosphate buffer and sodium acetate buffer; pain-killer, such as procaine hydrochloride; stabilizer, such as benzyl alcohol, phenol; and anti-oxidants. The prepared injection may be filled into a suitable ampule.

Methods well known to one skilled in the art may be used for administration to patients, for example, as intraarterial, intravenous, subcutaneous injections; and also as intranasal, transbronchial, intramuscular, percutaneous or oral administrations. The dosage of administration may vary according to the body-weight and age of the patient and the administration method; however, one skilled in the art can routinely select them.

The systemic expression of $p21^{Cip1}$ may provoke serious adverse effects because it may inhibit cell cycles essential for natural cell turnover. Moreover, systemic administration of compounds which increase $p21^{Cip1}$ expression may similarly cause side effects. Therefore, administration of $p21^{Cip1}$ and compounds increasing expression of $p21^{Cip1}$ is preferably conducted so as to limit the action of them to diseased parts such as joint. Thus, limiting the action to the diseased part by topical administration to joint, use of a drug delivery system, and so on can be considered.

For example, although there are some differences according to the symptoms, in general, the dose of a drug of the present invention is about 0.01 mg to about 1000 mg per day, preferably about 0.1 mg to about 100 mg per day and more preferably about 1.0 mg to about 50 mg per day, when administered orally to a normal adult (weight 60 kg).

When administering parenterally in the form of an injection to a normal adult (weight 60 kg), although there are some differences according to the target of administration, symptoms and method of administration, it is convenient to intravenously inject a dose of about 1 µg to about 100 mg per day, preferably about 0.01 to about 30 mg per day, and more preferably about 0.1 to about 20 mg per day.

In the case of using DNA which encodes the $p21^{Cip1}$ protein as therapeutic drug for the inhibition of aberrant growth of synovial tissue, inflammation of synovial tissue, and/or the expression of inflammatory cytokines in synovial tissue (in the case of gene therapy), DNA encoding the $p21^{Cip1}$ protein is incorporated into a suitable vector such as adenovirus vector, adeno-associated virus vector, retrovirus vector, plasmid DNA or the like, and is administered to patients. When adenovirus is used as the vector, it is desirable to use less inflammatory variants and such of the adenoviruses (Steinwaerder, D. S. et al., 1999, J. Virol. 73: 9303-9313). As for the administration method, desirable method can be properly selected from methods well known to one skilled in the art, for example, such as topical administration to diseased part, or the like, and are conducted. In vivo method is suitably used as the administration method. Moreover, ex vivo method can be used in the case of expecting paracrine effect from gene-transfected cells. The tissue transitivity and the tissue absorbency of the administration can be improved by enclosing the gene in the liposome which is produced by making phospholipids or such into micelle. Moreover, the tissue transitivity and the tissue absorbency can also be improved by adding cationic lipids to form complex with gene DNA. As a result, it is considered that aberrant growth of synovial tissue, inflammation of synovial tissue, and/or the expression of inflammatory cytokines in synovial tissue can be inhibited.

BRIEF DESCRIPTION OF THE DRAWINGS

FIGS. 3A-3J shows the effects of $p16^{INK4a}$ and $p21^{Cip1}$ gene therapy on CIA in mice. Mice with CIA were administered twice with AxCAp16, AxCAp21, AxCALacZ adenoviruses, or saline. Radiological (3A to 3E) and histopathological (3F to 3J) examination of the arthritic joints were performed 3 weeks after the second immunization. 3A and 3F, normal ankle joints; 3B and 3G, saline-administered CIA ankle joints; 3C and 3H, AxCALacZ-administered CIA ankle joints; 3D and 3I, AxCAp16-administered CIA ankle joints; 3E and 3J, AxCAp21-administered CIA ankle joints. 3F-3J, original magnification 35×.

FIGS. 9A-D show the effects of p21$^{Cip1}$ gene therapy on histopathology of AA. The arthritic joints that were transfected with the gene three times were histologically examined 4 weeks after the immunization. The synovial tissue sections around the patellar ligaments were stained with hematoxylin and eosin. 9A: the normal joint, 9B: the saline-administered joint, 9C: the AxCALacZ-administered joint, 9D: the AxCAp21-administered joint. p: patella, s: synovial tissue, f: femur, t: subpatellar tendon.

BEST MODE FOR CARRYING OUT THE INVENTION

Figure 1A:
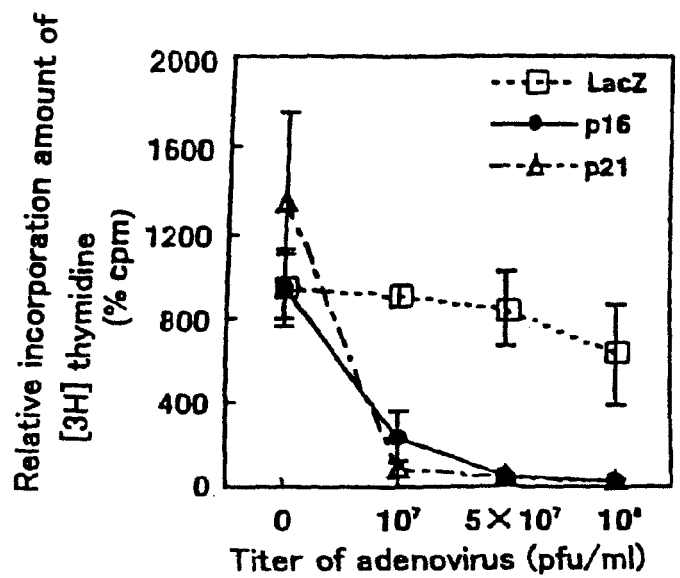
FIGS. 1A-B show the effects of $p16^{INK4a}$ and $p21^{Cip1}$ gene transfection on growth of rheumatoid synovial fibroblasts. Human synovial fibroblasts derived from rheumatoid synovial tissues of RA patients were infected with various titers of AxCAp16, AxCAp21, or AxCALacZ adenovirus, and stimulated with 10% FCS (1A), or 10 ng/ml PDGF plus 1% FCS (1B). [$^3$H]-TdR incorporation of the infected fibroblasts are shown in relation to that of control synovial fibroblasts that were uninfected and growth-stimulated. Inhibition of cell growth by gene transfection of $p16^{INK4a}$ (filled circles) or $p21^{Cip1}$ (open triangles), but not that of lacZ (open squares), showed a viral-titer-dependent manner. The points and bars in the graph represent the mean±SEM.

The present invention is illustrated in detail by the following Examples, but is not restricted to them.

Cultured rheumatoid synovial fibroblasts (RSFs) were prepared from rheumatoid synovial tissues from RA patients undergoing total joint replacement surgery or synovectomy at Nippon Medical School Hospital, Tokyo Metropolitan Bokutoh Hospital, or Fuchu Hospital. Consent forms were obtained from patients prior to the surgical procedures. RA was diagnosed according to the criteria of the American College of Rheumatology (Arnett, F. C. et al., 1988, Arthritis Rheum. 31: 315-324). The synovial fibroblasts were cultured as described previously (Taniguchi, K. et al., 1999, Nature Med. 5: 760-767). Statistical analyses described in Example 2 were performed with StatView 4.5J software (Abacus Concepts, Berkeley, Calif.). Statistical differences of the ankle width and the paw volume of the CIA mice were assessed by Student's t test and the disease scores by the Mann-Whitney U test (see Example 2). Statistical analyses described in Example 4 to 7 were carried out with StatView-5.0 J software (SAS Institute Inc., Cary, N.C.). The $^3$H-thymidine uptake of the cultured RSF, as well as knee width, thickness of the cartilage and synovial membranes, and PCNA-LIs of the AxCAp21-administered and AxCALacZ-administered joints were compared with a paired t-test (see Example 6 and 7). The scores of pannus invasion were compared with a Mann-Whitney U test (see Example 7). The percentages of the apoptotic RSF infected with the adenoviruses were compared in a t-test (see Example 5).

EXAMPLE 1

Transfection of Adenoviral Vectors Incorporated with p16$^{Ink4a}$ and p21$^{Cip1}$ Gene Inhibits Synovial Cell Proliferation The anti-proliferative effects of the forced expression of p21$^{Cip1}$ as well as p16$^{INK4a}$ on the synovial cells were examined using human synovial fibroblasts. RSFs prepared from the rheumatoid synovial tissues were infected with the recombinant adenoviruses AxCAp16, AxCAp21, or AxCA-LacZ, containing p16$^{INK4a}$, p21$^{Cip1}$, or E. coli lacZ, respectively. Replication-defective adenoviruses containing a human p16$^{INK4a}$ gene and a human p21$^{Cip1}$ gene (AxCAp16 and AxCAp21, respectively) were kindly supplied by Drs. Terada and Ito (Tokyo Medical and Dental University, Tokyo, Japan) (Terada, Y. et al., 1997, J. Am. Soc. Nephrol. 8: 51-60). A recombinant adenovirus encoding the lacZ gene (AxCA-LacZ) was kindly provided by Dr. Saito (University of Tokyo, Tokyo, Japan) (Kanegae, Y. et al., 1995, Nucleic Acids Res. 23: 3816-3821). High-titer recombinant adenoviruses were prepared by amplification in 293 cells and purified by cesium chloride density-gradient centrifugation (Kanegae, Y. et al., 1994, Jpn. J. Med. Sci. Biol. 47: 157-166). Their growth was stimulated with 10%. FCS or 10 ng/ml platelet-derived growth factor (PDGF), and cell proliferation was assessed by measuring [$^3$H]-Tdr incorporation. In vitro gene transfection of the recombinant adenoviruses and measurement of [$^3$J]-Tdr incorporation by the adenovirus-infected cells are described in the literature (Terada, Y. et al., 1997, J. Am. Soc. Nephrol. 8: 51-60).

Figure 1B:
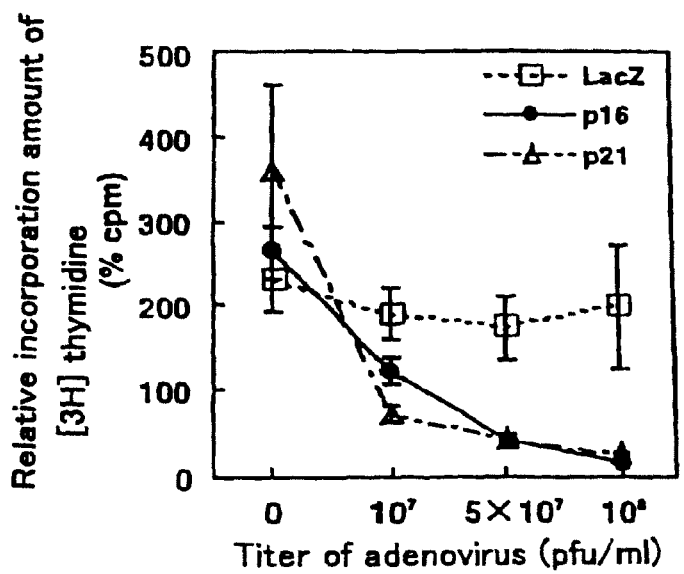

When the synovial cells were infected with the AxCAp16 or AxCAp21, their proliferation was suppressed in a viral-titer-dependent manner (FIG. 1). No effects were observed with AxCALacZ. Similar growth-suppressive effects were seen when murine NIH3T3 fibroblastoid cells were infected with the same viruses and stimulated in the same manner.

EXAMPLE 2

Effects of p16$^{Ink4a}$ and p21$^{Cip1}$ Gene Induction on the Pathology of CIA The same set of adenoviruses as in Example 1 was used to induce the p16$^{INK4a}$, p21$^{Cip1}$, or lacZ gene in vivo in the synovial tissues of CIA mice.

Induction of CIA was performed as follows. Male DBA/1J mice were purchased from Japan Charles River Laboratories (Tokyo, Japan) and housed in the Tokyo Medical and Dental University Animal Research Center. Bovine type II collagen (Collagen Research Center, Tokyo, Japan) was dissolved at 2 mg/ml in 0.1 M acetic acid, then was emulsified with an equal volume of complete Freund's adjuvant (Iatron, Tokyo, Japan). A hundred microliter of the immunogen was injected intradermally into 8-weeks-old mice at the tail base. After 3 weeks, the mice received the same antigen subcutaneously. Arthritis was developed within 10 days of the second immunization.

In vivo gene transfection into the joints was performed either on the same day as the second immunization and 10 days later, or only 10 days after the second immunization. More specifically, AxCAp16, AxCAp21, and AxCALacZ adenoviruses were prepared at a concentration of 10$^8$ particles/µl in saline. Each mouse received bilateral intraarticular injection at the ankle joints (5 µl per joint) and the knee joints (10 µl per joint), and bilateral periarticular injection at the tarsal joints (5 µl per joint), simultaneously. Injection of saline alone served as a control.

The assessment of CIA disease severity, the severity of the arthritis at each hind leg, was scored as follows: 0, normal; 1, erythema and mild swelling confined to the ankle joint or toes; 2, those extending from the ankle to the midfoot; 3, erythema and severe swelling extending from the ankle to the metatarsal joints; 4, ankylosing deformation with joint swelling (Rosloniec, E. F. et al., 1996, Collagen-induced arthritis, In Current Protocols in Immunology., J. E. Coligan et al. eds., John Wiley & Sons, Inc., NY., 15.5.1-24). The disease score for each mouse represented the sum of the scores for the two hind legs. Scoring was performed by two examiners in a blind test. The ankle width was measured with a micrometer (Ozaki Manufacturing, Tokyo, Japan), and the paw volume with a TK101 plethysmometer (Unicorn, Chiba, Japan). Radiographs of the hind legs were taken by direct exposure on X-ray film (Fuji Photo Film Co., Tokyo, Japan) at 3.5 mA for 1 min using an SRO-M30 X-ray machine (Sofron, Tokyo, Japan).

Figure 2A:
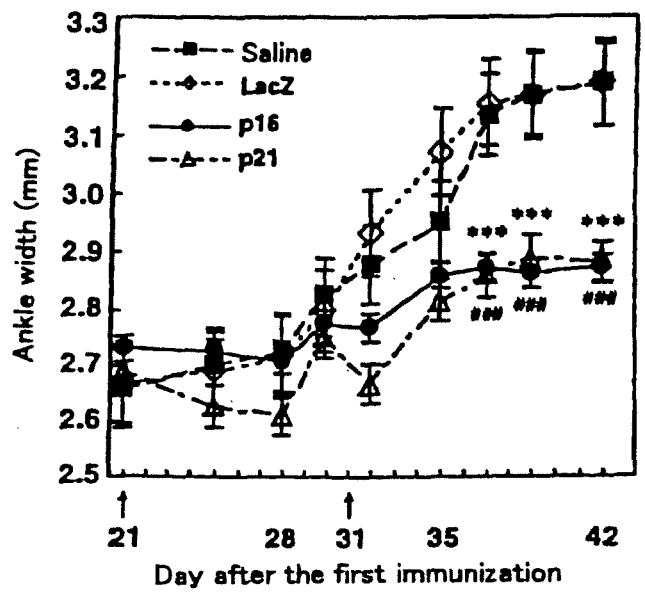
FIGS. 2A-D shows the effects of $p16^{INK4a}$ and $p21^{Cip1}$ gene therapy on progression of CIA. Mice with CIA were administered with AxCAp16 (filled circles), AxCAp21 (open triangles), AxCALacZ (open diamonds) adenoviruses, or saline (filled squares) either twice (arrows, on days 21 and 31) (2A, 2B, and 2C) or once after the onset of arthritis (arrow, on day 31) (2D). The ankle width (2A), paw volume (2B), and disease score (2C and 2D) of the animals were measured on the indicated days. The points and bars in the graph represent the mean±SEM of seven mice. *P<0.05, P<0.01, *P<0.001 [$p16^{INK4a}$ (AxCAp16) versus saline]. #p<0.05, ##p<0.01, ###p<0.001 [$p21^{Cip1}$ (AxCAp21) versus saline].
Figure 2B:
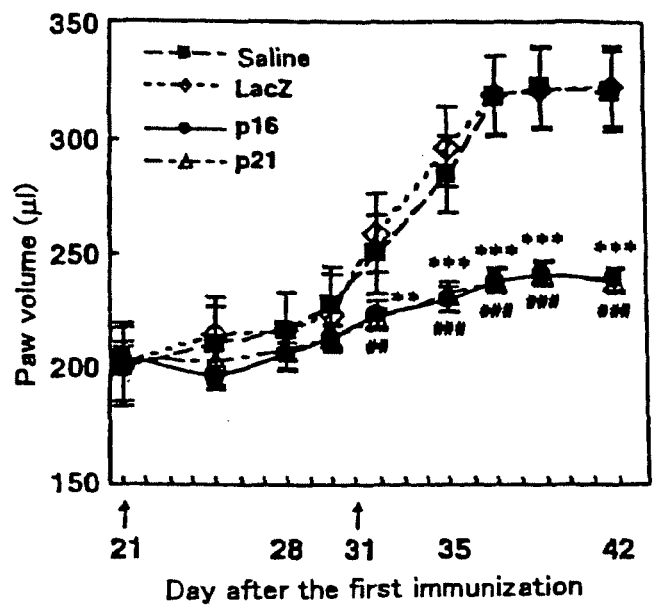
Figure 2C:
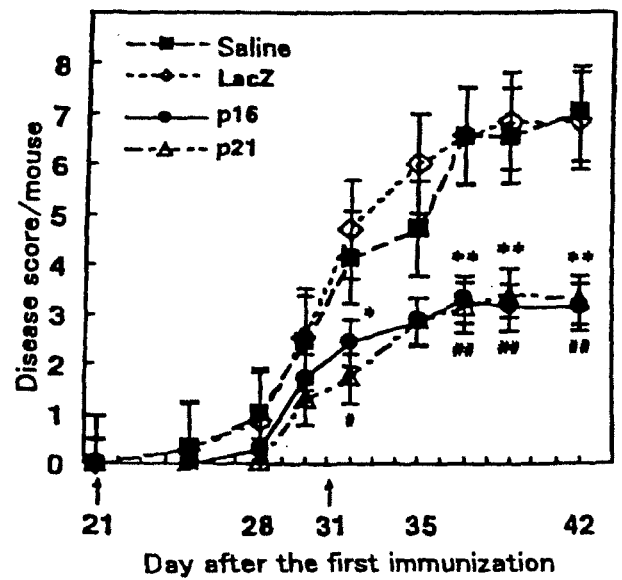

AxCAp16, AxCAp21, and AxCALacZ adenoviruses were injected to the ankle joints of the mice. RNA was prepared from these mice and reverse-transcribed to complimentary DNA (cDNA) with reverse transcriptase. Using the cDNAs as templates, reverse transcription (RT)-PCR was carried out with specific primers. The mRNAs of the transfected genes were expressed specifically in the joints receiving the recombinant adenoviruses with the corresponding genes. During the course of the disease, the ankle width, paw volume, and disease score were assessed by physical examination. In comparison with saline injection or lacZ gene transfection, p16$^{INK4a}$, or p21$^{Cip1}$ gene transfection significantly ameliorated the arthritis (FIGS. 2A, B and C). The swelling of the knee joints was also suppressed in the CDKI-administered mice. The differences in the disease scores reached statistical significance (P<0.05) 11 days after the first gene transfection.

The onset of the disease was delayed 2.4 days on average in the AxCAp16-administered mice and 3.4 days on average in the AxCAp21-administered mice, in comparison with the saline-administered mice.

Figure 2D:
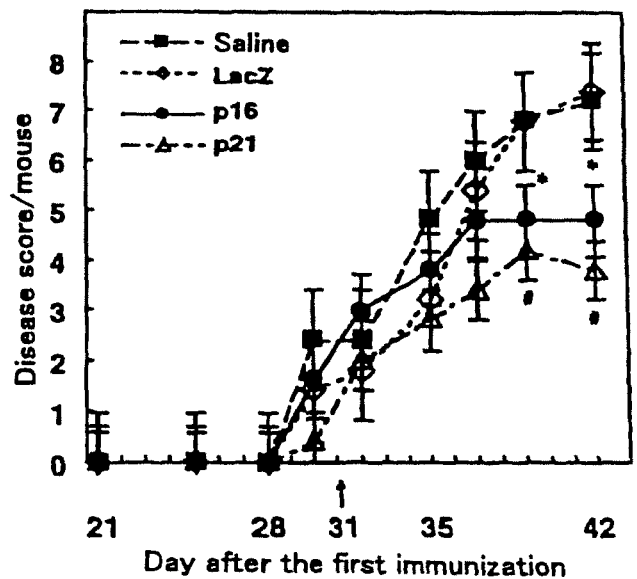

The therapeutic effects of CDKI gene transfection after the onset of arthritis were studied by administrating the CIA mice 10 days after the second immunization when joint swelling had become evident. Administration with either AxCAp16 or AxCAp21 significantly suppressed the progression of the arthritis even after it had already developed (FIG. 2D).

3 weeks after the second immunization, radiological examination of the ankle joints revealed that tissue swelling and bone erosion were markedly inhibited in the joints of the CDKI-administered mice (FIG. 3A to E). At the same time, the administered ankles were histologically examined (FIG. 3F to J). Hind paws from CIA mice taken 3 weeks after the second immunization were fixed in 10% phosphate-buffered formalin (pH 7.4), decalcified in 10% EDTA, and embedded in paraffin for histological examination. Sections (4 µm) were stained with haematoxylin and eosin. Joints administered with AxCAp16 or AxCAp21 exhibited greatly reduced synovial hyperplasia compared with joints administered with AxCALacZ or saline (FIGS. 3I and J). The infiltration of mononuclear cells into the synovial tissues and the formation of pannus were diminished, and no destruction of the cartilage or bone was seen.

In all of the clinical and histological aspects examined by the present inventors, no significant differences were observed between joints administered with AxCAp16 and those administered with AxCAp21.

EXAMPLE 3

Effects of p16$^{Ink4a}$ and p21$^{Cip1}$ Gene Induction on the Expression of Pro-Inflammatory Cytokines in the CIA-Affected Joints As in the case of RA, TNF-α and IL-1, which are mainly secreted from the synovial cells, largely account for the pathology of CIA (Piguet, P. F. et al., 1992, Immunology 77: 510-514; Williams, R. O. et al., 1992, Proc. Natl. Acad. Sci. USA. 89: 9784-9788; Wooley, P. H. et al., 1993, J. Immunol. 151: 6602-6607; Joosten, L. A. B. et al., 1996, Arthritis Rheum. 39: 797-809). Thus, the inventors studied the expression of the pro-inflammatory cytokines, IL-1β, IL-6, and TNF-α, in arthritic joints administered with AxCAp16, AxCAp21, AxCALacZ adenovirus, or saline. The synovial tissues from the hind paws were collected on the day of histopathological examination. mRNA expression levels of these cytokines were analyzed by RT-PCR.

Total RNA was extracted from the arthritic synovial tissues with Isogen (Nippongene Co., Tokyo, Japan) for RT-PCR analysis. cDNA was synthesized with Superscript II reverse transcriptase (Life Technologies, Gaithersburg, Md.) and subjected to 25 cycles of PCR to amplify glyceraldehyde-3-phosphate dehydrogenase (GAPDH), or 30 cycles of PCR to amplify human p16$^{INK4a}$ and p21$^{Cip1}$, E. coli lacZ, mouse IL-1β, IL-6, and TNF-α cDNA. The PCR cycle was 94° C. for 1 min, 58° C. for 1 min, and 72° C. for 2 min. The products were fractionated by agarose gel electrophoresis and stained with ethidium bromide. The nucleic acid sequences of the specific PCR primers were as follows: human p16$^{INK4a}$, 5'-AAC GCA CCG AAT AGT TAC GG-3' (sense) (SEQ NO ID: 1) and 5'-GCA TGG TTA CTG CCT CTG GT-3' (antisense) (SEQ NO ID: 2); human p21$^{Cip1}$, 5'-ACT GTG ATG CGC TAA TGG C-3' (sense) (SEQ NO ID: 3) and 5'-ATG GTC TTC CTC TGC TGT CC-3' (antisense) (SEQ NO ID:

4); E. coli lacZ, 5'-ACT TAA TCG CCT TGC AGC AC-3' (SEQ NO ID: 5) (sense) and 5'-CAT CTG AAC TTC AGC CTC CA-3' (antisense) (SEQ NO ID: 6); mouse IL-1β, 5'-CTG AAA GCT CTC CAC CTC-3' (sense) (SEQ NO ID: 7) and 5'-GGT GCT GAT GTA CCA GTT GG-3' (antisense) (SEQ NO ID: 8); mouse IL-6,5'-GAG ACT TCC ATC CAG TTG CC-3' (sense) (SEQ NO ID: 9) and 5'-TTC TGC AAG TGC ATC ATC G-3' (antisense) (SEQ NO ID: 10); mouse TNF-α, 5'-GCC ACC ACG CTC TTC TG-3' (sense) (SEQ NO ID: 11) and 5'-ATG GGC TCA TAC CAG GG-3' (antisense) (SEQ NO ID: 12); mouse GAPDH, 5'-AAG AAG GTG GTG AAG CAG GC-3' (sense) (SEQ NO ID: 13) and 5'-TCC ACC ACC CTG TTG CTG TA-3' (antisense) (SEQ NO ID: 14).

Figure 4:
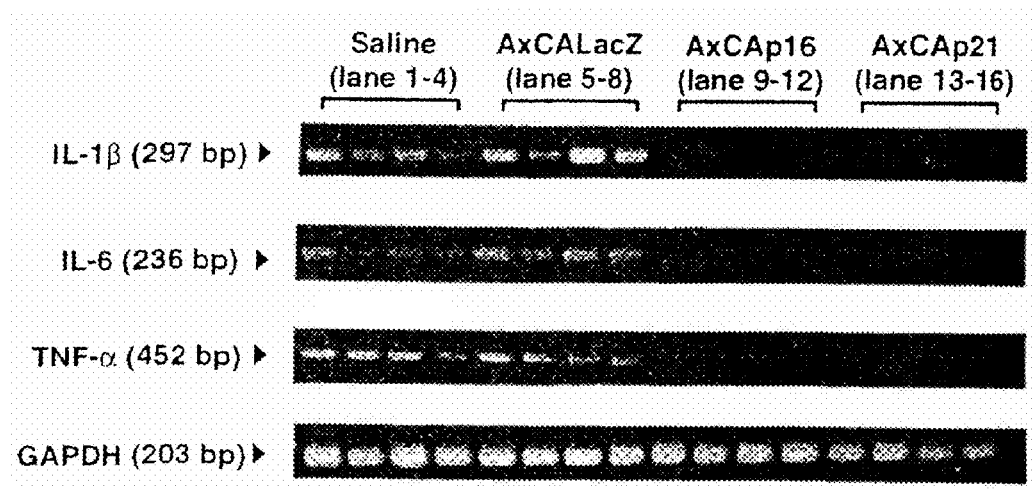
FIG. 4 shows the effects of $p16^{INK4a}$ and $p21^{Cip1}$ in vivo gene transfection on expression of pro-inflammatory cytokine mRNAs in the CIA joints. The joints were administered twice with AxCAp16, AxCAp21, AxCALacZ adenoviruses, or saline. The hind paw synovial tissues of 4 mice from each group taken 3 weeks after the secondary immunization were examined for the expression of mRNAs for IL-1β, IL-6, TNF-α, and GAPDH. The expected product size of each RT-PCR assay is shown in parentheses. Lanes 1 to 4, saline-treated ankle joints; lanes 5 to 8, AxCALacZ-administered ankle joints; lanes 9 to 12, AxCAp16-administered ankle joints; lanes 13 to 16, AxCAp21-administered ankle joints.
Figure 5:
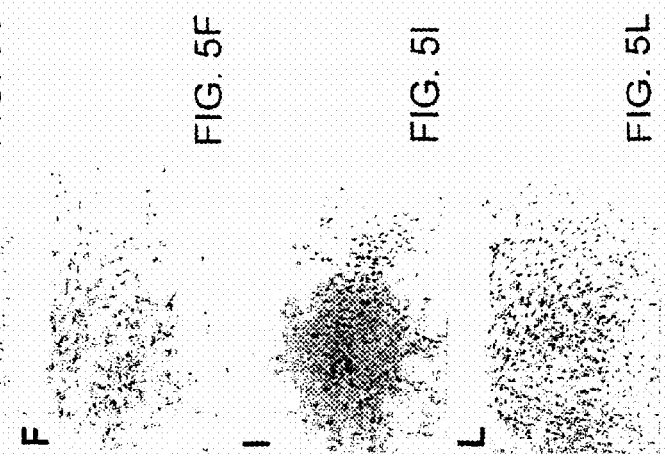
FIGS. 5A-5L show the results of immunohistochemical analyses of IL-1β and TNF-α in the synovial tissues of the CIA joints. The synovial tissues of the CIA knee joints administered twice with AxCAp16 (5G-5I), AxCAp21 (5J-5L), AxCALacZ (5D-5F), or saline (5A-5C) were collected for the preparation of serial cryostat sections. Tissues were administered with anti-TNF-α Ab (5A, 5D, 5G, and 5J), Ab (5B, 5E, 5H, and 5K), or normal rabbit serum (NRS) (5C, 5F, 5I, and 5L). Bound antibodies were visualized with horseradish peroxidase and its substrate, DAB. Because of saponin administration, IL-1β and TNF-α were stained primarily around the nucleus. Original magnification 140×.

All of the cytokine mRNAs were detected abundantly in the AxCALacZ- and saline-administered synovial tissues (FIG. 4). In contrast, they were undetectable or present at only very low levels in synovial tissues administered with AxCAp16 or AxCAp21. The amount of the mRNA was standardized with that of the extracted RNA. GAPDH mRNA was equally amplified from the joints of each group.

Next, the inventors performed immunohistochemical analysis to identify cells expressing IL-1β or TNF-α in the synovial tissues.

The synovial tissues from knee joints of hind legs of CIA mice taken 3 weeks after the second immunization were embedded in ornithine carbamyl transferase compound (Tissue-Tek; Miles, Elkhart, Ind.), frozen in liquid nitrogen, and stored at −80° C. Serial cryostat sections (8 μm) were air-dried, fixed with cold 4% phosphate-buffered paraformaldehyde (pH 7.4) washed with 10 mM Tris-HCl (pH 7.5) containing 150 mM NaCl and 0.1% saponin, and incubated with 10% normal goat serum. They were then incubated with rabbit anti-human IL-1β (LP-712; Genzyme, Cambridge, Mass.), rabbit anti-mouse TNF-α Ab (IP-400; Genzyme), or normal rabbit serum overnight at 4° C. They were then incubated with biotinylated goat anti-rabbit IgG (Southern Biotechnology Associates, Birmingham, Ala.), treated with 0.3% hydrogen peroxide in methanol, and incubated with horseradish peroxidase-labeled streptavidin (Vector Laboratories, Burlingame, Calif.). Bound antibodies were visualized with 0.5 mg/ml 3,3'-diaminobenzidine tetrahydrochloride in PBS (pH 7.4) and 0.02% hydrogen peroxide, and finally, were counterstained with hematoxylin.

In the joints administered with AxCALacZ or saline, these cytokines were found strongly in the synovial lining layer and also in the intimal synovial tissues (FIG. 5A to F). In contrast, with the same staining procedures, IL-1β or TNF-α staining in the synovium of the AxCAp16- and AxCAp21-administered joints was very weak (FIG. 5G to L). Thus, gene transcription and release of the pro-inflammatory cytokines in the synovial tissues were markedly down-regulated in the CDKI-administered joints.

EXAMPLE 4

Growth Inhibition of RSF by the p21$^{Cip1}$ Gene Transfection

Using AxCAp21 recombinant adenoviruses described above, effect of the ectopic expression of p21$^{Cip1}$ on proliferation of RSF was evaluated. An Ax1w1 adenovirus without insertion was purchased from the Riken Gene Bank (Saitama, Japan) and used as the control. Synovial tissues were obtained from 5 RA patients, under their consent, who underwent synovectomy or total knee joint replacement surgery for active rheumatoid synovitis at Nippon Medical School Hospital, Tokyo Metropolitan Bokuto or Huchu Hospital. They all fulfilled the American College of Rheumatology criteria for classification of RA (Arnett, F. C. et al., 1988, Arthritis & Rheum. 31: 315-324). RSF were isolated and cultured as described elsewhere (Taniguchi, K. et al., 1999, Nature Med. 5: 760-767).

Figure 6:
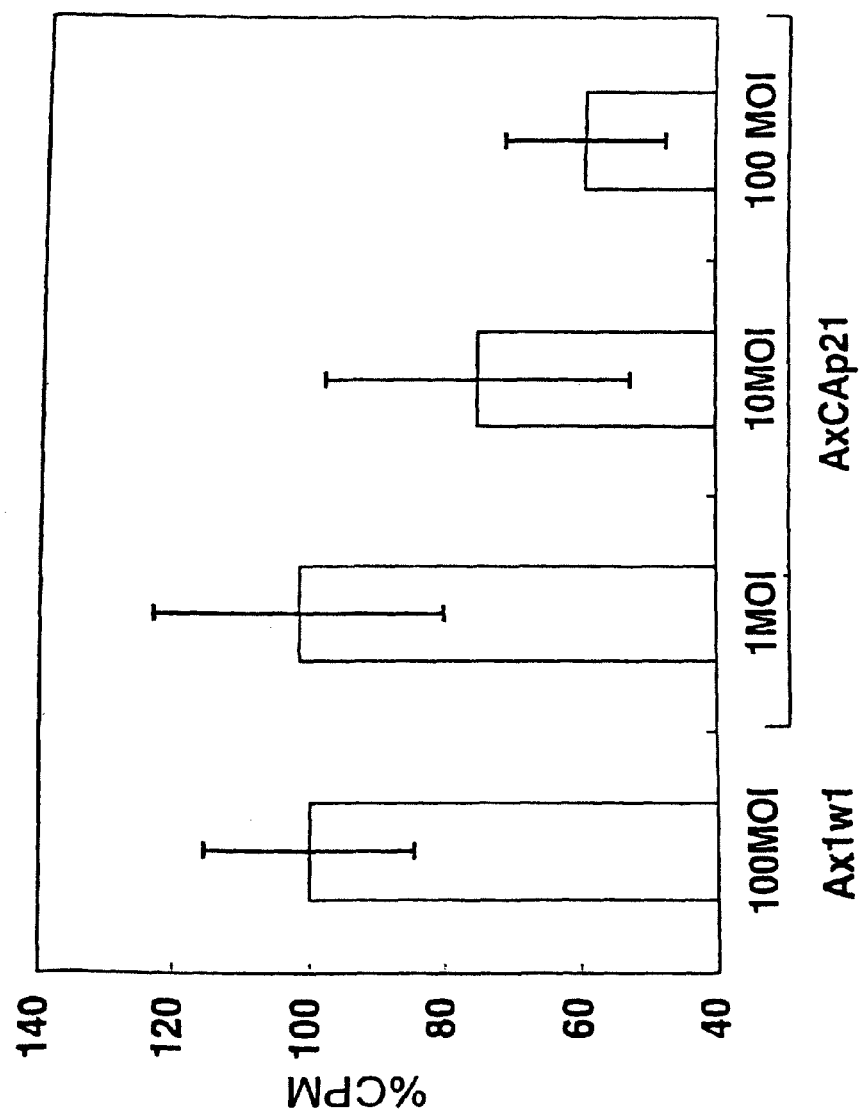
FIG. 6 shows the growth inhibition of the RSF by the p21$^{Cip1}$ gene transfection. RSF infected with the indicated MOI of the Ax1w1 or AxCAp21 adenoviruses were stimulated with 10% FBS. $^3$H-thymidine incorporation by AxCAp21-infected RSF is shown in relation to that of control RSF infected with Ax1w1. Statistically significant difference (P<0.01) was exhibited by 100 MOI infection.

RSF were cultured to allow logarithmic growth with media containing 10% FBS. They were infected with the AxCAp21 adenoviruses containing the human p21$^{Cip1}$ gene or with the Ax1w1 adenoviruses containing no insert genes. In vitro adenoviral infection was conducted as described previously (Terada, Y. et al., 1998, J. Am. Soc. Nephrol. 9: 2235-2243). Western blot analysis of the total cell lysates of the infected cells showed that the p21$^{Cip1}$ protein was expressed specifically by the AxCAp21-infected cells but not by the Ax1w1-infected cells. Proliferations of the cells were evaluated 24 hours after the infection. Cell growth was assessed by incorporation of $^3$H-thymidine (Taniguchi, K. et al., 1999, Nature Med. 5: 760-767). Compared to the proliferation of the Ax1w1-infected RSF, that of the AxCAp21-infected RSF was significantly suppressed. The suppressive effect depended on the titer of the viruses (FIG. 6).

EXAMPLE 5

Apoptotic Cell Death of RSF with the Overexpressed p21$^{Cip1}$ Gene

Growth inhibition observed in the AxCAp21-infected RSF could be due to apoptosis induced by the ectopic p21$^{Cip1}$ expression. Thus, RSF infected with the AxCAp21 adenoviruses and those infected with the Ax1w1 adenoviruses were examined for apoptotic cell death.

A half million RSF were infected with 5×10$^7$ PFU of the AxCAp21 or Ax1w1 adenoviruses at 100 MOI. To induce apoptosis, the same number of cells were treated with 50 μM N-acetylsphingosine (Wako Pure Chemical industries, Osaka, Japan) in RPMI1640 medium supplemented with 40 ng/ml PDGF (Genzyme, Cambridge, Mass.) (Mizushima, N. et al., 1998, Ann. Rheum. Dis. 57: 495-499). After 4 days, the treated cells were isolated with trypsin-EDTA solution (Immunobiology Laboratories, Gunma, Japan), fixed with 1% glutaraldehyde in PBS, and stained with Hoechst 33258 (Molecular Probes, Eugene, Oreg.). To quantify the apoptotic cells, 500 nuclei were visually examined. Total cellular DNA were extracted from the treated cells and the fragmentation of the DNA was analyzed with 2% agarose gel DNA electrophoresis.

Figure 7A:
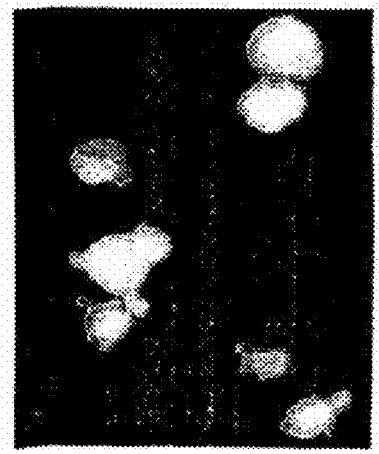
FIGS. 7A-7E show the results of apoptosis assays of RSF with forced p21$^{Cip1}$ expression. 7A, 7B, 7C, and 7D: Hoechst 33258 staining of the nuclei. RSF treated with N-acetylsphingosine displayed nuclear condensation and fragmentation characteristic of the apoptotic cells (7A). The AxCAp21-treated RSF (7B) and Ax1w1-treated RSF (7C), as well as the non-treated RSF (7D), showed no signs of apoptosis. (Original magnification ×400.) See Examples for quantitation of the apoptotic cells. 7E: Agarose gel electrophoresis of cellular DNA. Total cellular DNA of non-treated RSF (lane 2), RSF 2 days (lane 3) and 4 days (lane 4) after the AxCAp21 infection, and RSF 2 days (lane 5) and 4 days (lane 6) after the Ax1w1 infection were analyzed. The DNA of UV-treated HL-60 cells was fractionated to show typical nucleosomal DNA ladder (lane 7). Lane 1: DNA molecular weight marker (φX174 HaeIII digests).
Figure 7B:
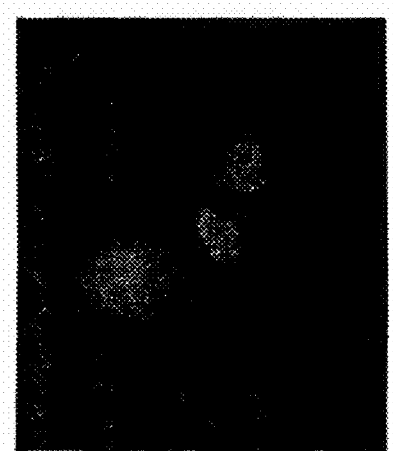
Figure 7C:
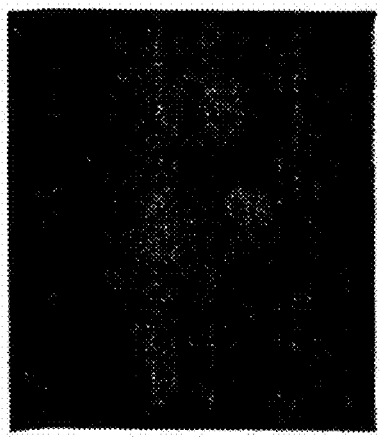
Figure 7D:

As reported previously, RSF underwent apoptotic cell death when they were treated with N-acetylsphingosine (Mizushima, N. et al., 1998, Ann. Rheum. Dis. 57: 495-499). The apoptotic RSF displayed characteristic morphological changes such as nuclear condensation and fragmentation when they were stained with Hoechst 33258 (FIG. 7A). The RSF treated with a growth-inhibitory concentration (100 MOI) of AxCAp21 or those with the same dose of Ax1w1 were also stained 4 days after the infection (FIGS. 7B and C). They were compared with RSF cultured without virus infection (FIG. 7D). The percentages of apoptotic cells that showed characteristic nuclear changes were evaluated in three different samples for each type of infection. The frequencies of the apoptotic cells in the non-infected, AxCAp21-infected, and Ax1w1-infected RSF were not significantly different (0.52±0.45%, 0.69±0.60%, and 0.60±0.67%, respectively).

Figure 7E:

Nuclear DNA of RSF infected with the AxCAp21 or Ax1w1 control viruses were fractionated with agarose gel electrophoresis. Whereas DNA of the apoptotic HL-60 cells had typical nucleosomal DNA ladders, the AxCAp21-infected or Ax1w1-infected RSF had no fragmented DNA (FIG. 7E). These results suggest that the p21$^{Cip1}$ over-expression did not induce apoptotic cell death of RSF. These results demonstrate that forced expression of the p21$^{Cip1}$ gene inhibits cell growth of RSF without inducing their apoptotic cell death.

EXAMPLE 6

Administration of Rat AA with Adenoviral p21$^{Cip1}$ Gene Transfection

Six 6-week-old male Lewis rats were immunized with 1 mg of *M. butyricum* emulsified in 100 μl of mineral oil to induce AA. Rats were given injection of AxCAp21 into the right knees and that of AxCALacZ into the left knees. The intraarticular gene transfection to the knee joints was carried out by injecting 1×10$^7$ PFU of the adenoviruses in 50 μl of saline. The gene transfection was carried out once (7 days after the immunization) or three times (8, 15, and 22 days after the immunization). During the course of the disease, severity of the arthritis was clinically scored (Eden, W. and Josee, P. A., Adjuvant arthritis in rat. In: Current protocols in immunology. New York: John Wiley & Sons; 1996. Supplement 19). Width of the knee joints was measured by a micrometer. At the end of the clinical observation, the joints were fixed for histological and immunohistochemical analyses. Injections of saline alone served as a control.

Figure 8A:
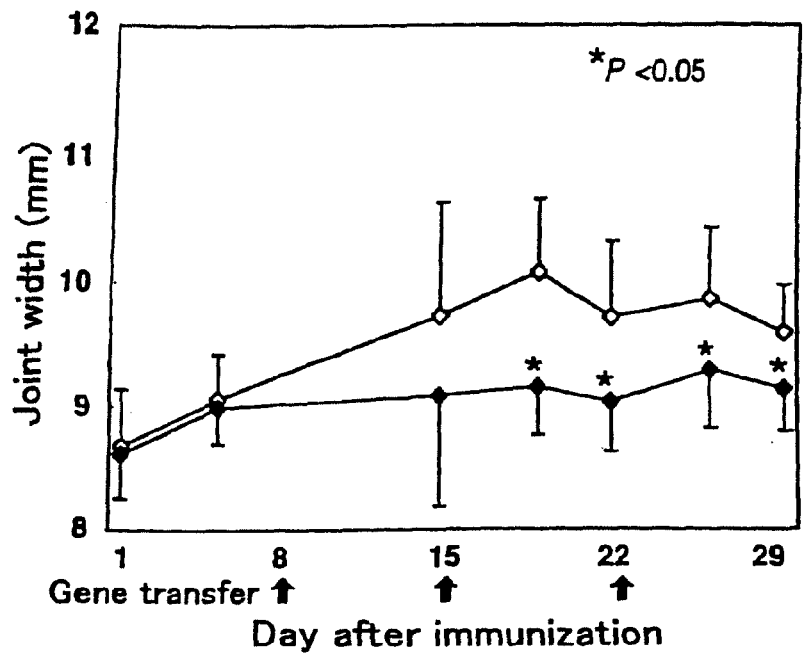
FIGS. 8A-B show the effects of the p21$^{Cip1}$ gene transfection on the joint swelling of rats with AA. The knee joints of rats with AA were administered with intraarticular injection of the AxCAp21 (filled diamonds) or AxCALacZ (open diamonds) adenoviruses. The points and bars represent the mean±SEM of 6 rats. Arrows represent the timing of the gene transfection. The gene transfection was carried out three times (8A) or once (8B). The asterisks represent statistically significant differences (P<0.05) between the two groups.
Figure 8B:
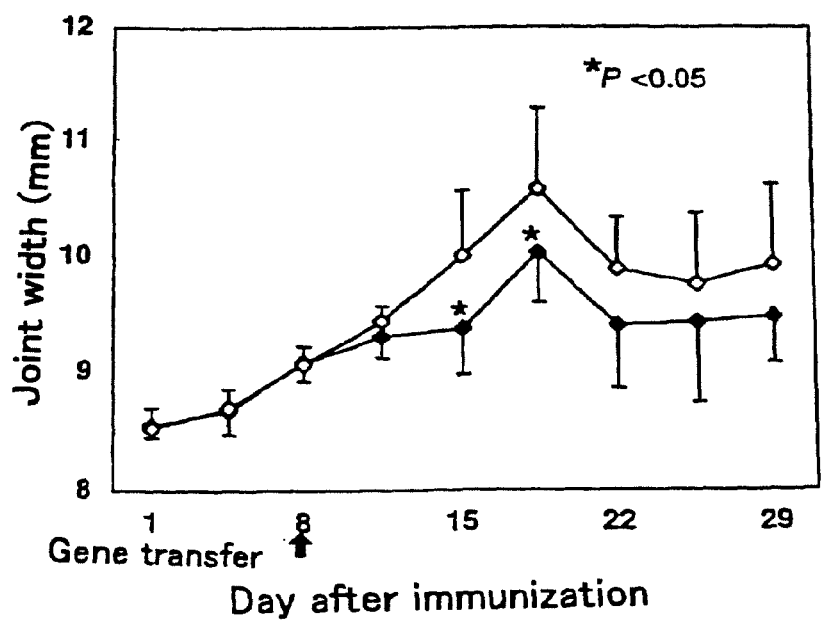
Figure 10A:
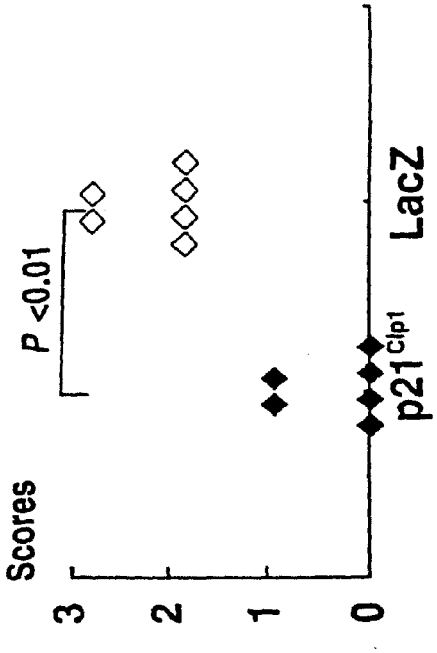
FIGS. 10A-10D show the results of histological measurements of the p21$^{Cip1}$-administered knee joints. The joints administered with the AxCAp21 (p21$^{Cip1}$) or with AxCA-LacZ (LacZ) were examined for synovial thickness (10A), mononuclear cell infiltration (10B), pannus invasion (10C), and cartilage thickness (10D) by microscopy. The points and bars represent the mean±SEM derived from 6 rats (10A, 10B, 10D). The points in panel 10C represent the histological scores of the individual rats. The differences of all measurements were statistically significant.
Figure 10B:
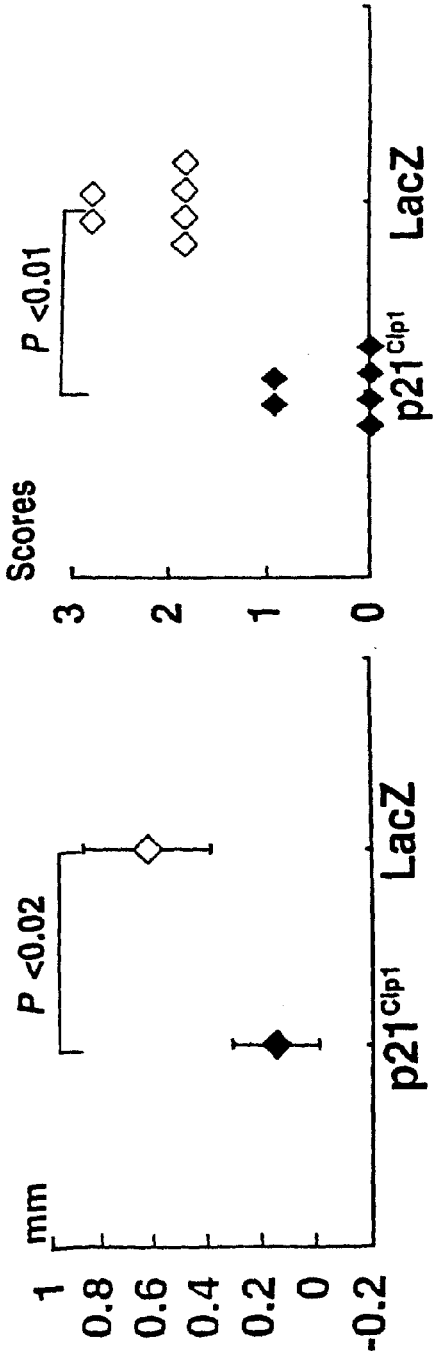
Figure 10C:
Figure 10D:
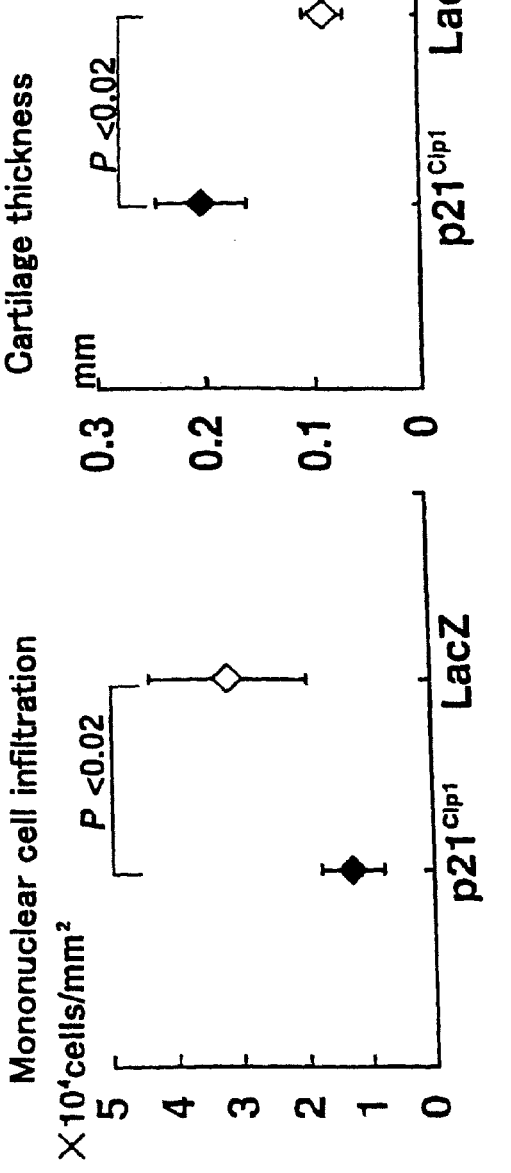

Swelling of the knee joints was monitored during the disease course. Arthritis developed in all rats around 10 days after the immunization. Without the administration, the knee joints width became maximal around 20 days after the immunization, and decreased afterwards. The decline was due to fibrosis of the joints and atrophy of the adjacent muscles. The knee joints administered with the control adenoviruses followed the same course (FIG. 8). In comparison, swelling of the knees of the p21$^{Cip1}$ gene transfected rats was significantly suppressed, whether the gene transfection was conducted once or three times (FIG. 8, P<0.05). The therapeutic effect lasted throughout the experiment to a statistically significant extent when the transfections of the gene were repeated three times with an interval of one week between transfections. This finding clearly shows that the intraarticular gene transfection of p21$^{Cip1}$ ameliorates the adjuvant arthritis in rat in vivo. Although the gene transfection carried out once also suppressed the joint swelling effectively, the effect decreased after 2 weeks from the gene transfection.

EXAMPLE 7

Effects of the p21$^{Cip1}$ Gene Transfection on Histopathology of Rat AA

The joints of the rats, which were subjected to gene transfection treatment three times, were histologically examined a week after the last transfection. The knee joints were embedded in paraffin wax after 10% PBS-formalin fixation and decalcification. Their sections (5 μm) were stained with hematoxylin and eosin. Thickness of the synovial tissues and cartilage was measured at the position close to the synovial attachment to the tibial head. Mononuclear cells in 1.8×10$^{-8}$ m$^2$ of the synovial tissues were enumerated at the same position. Severity of the pannus invasion was scored as was done previously (Taniguchi, K. et al., 1999, Nature Med. 5: 760-767).

The synovial tissues of the knee joints from normal rats have one or two layer of synovial lining cells that were supported by loose fatty connective tissues (FIG. 9A). The arthritic joints administered with AxCALacZ or with saline had marked synovial thickening, which was accompanied by mononuclear cell infiltration. Also, destructive pannus tissues developed and invaded the adjacent bones (FIGS. 9B and C). The cartilage of the affected joints was degenerated. In contrast, synovial thickening and mononuclear cell infiltration were markedly suppressed in the synovial tissues of the AxCAp21-administered joints (FIG. 9D). Bone destruction by the pannus tissues was suppressed and cartilage was well preserved. Synovial thickness and cartilage thickness were measured, and infiltrated mononuclear cells were enumerated (Taniguchi, K. et al., 1999, Nature Med. 5: 760-767). Pannus invasion was scored for the severity. All of these measurements of the AxCAp21-administered and control LacZ (AxCALacZ)-administered joints showed that the p21$^{Cip1}$ gene transfection significantly ameliorated the arthritis (FIG. 10).

The cells in the S phase of cell cycle express PCNA. A week after gene transfection, the PCNA expression of arthritic synovial tissues was examined immunohistochemically.

For immunohistochemical analyses, the fixed sections (5 μm) were deparaffinized and treated by two rounds of microwave heating for 5 minutes in 10 μM sodium citrate (pH 6). The sections were incubated with 0.3% H$_2$O$_2$, with 10% normal goat serum in PBS, and with anti-PCNA monoclonal antibody (PC10, Santa Cruz Biotech, California) for 1 hour. This antibody reacts with a PCNA peptide chain distinct from the binding site for p21$^{Cip1}$, ruling out the possibility that binding of p21$^{Cip1}$ to PCNA interferes the antibody reactivity (Roos, G. et al., 1993, Lab. Invest. 68: 204-210; Chen, J. et al., 1996, Nucleic Acids Res. 24: 1727-1733). They were subsequently incubated with a biotinylated goat anti-mouse IgG antibody (AP181B, Chemicon International Inc, Temecula, Calif.), and with horseradish peroxidase-labeled streptavidin (Southern Biotechnology Associates Inc, Birmingham, Ala.). Bound antibodies were visualized with 0.02% 3,3'-diaminobenzidine tetrahydrochloride. The sections were counterstained with hematoxylin. The percentages of the PCNA-positive cells in total cells (PCNA labeling indices; LIs) were calculated by examining 200 synovial cells (Galand, P. and Degraef, C., 1989, Cell & Tiss. Kinet. 22: 383-392).

Figure 11A:
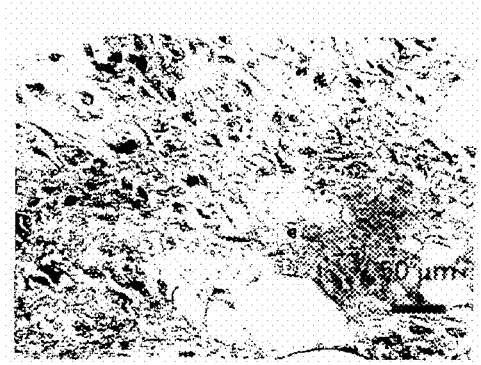
FIGS. 11A-C shows PCNA expression in the synovial tissues of the p21$^{Cip1}$-administered joints. The PCNA expression in the synovial tissues from the AxCAp21- (11A) and in AxCALacZ- (11B) administered joints was detected with an anti-PCNA monoclonal antibody. PCNA LIs were calculated and are shown as columns and bars, representing the mean±SEM (11C). The difference was statistically significant (P<0.01).
Figure 11B:
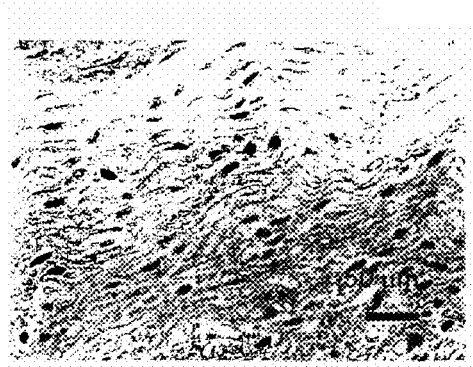
Figure 11C:
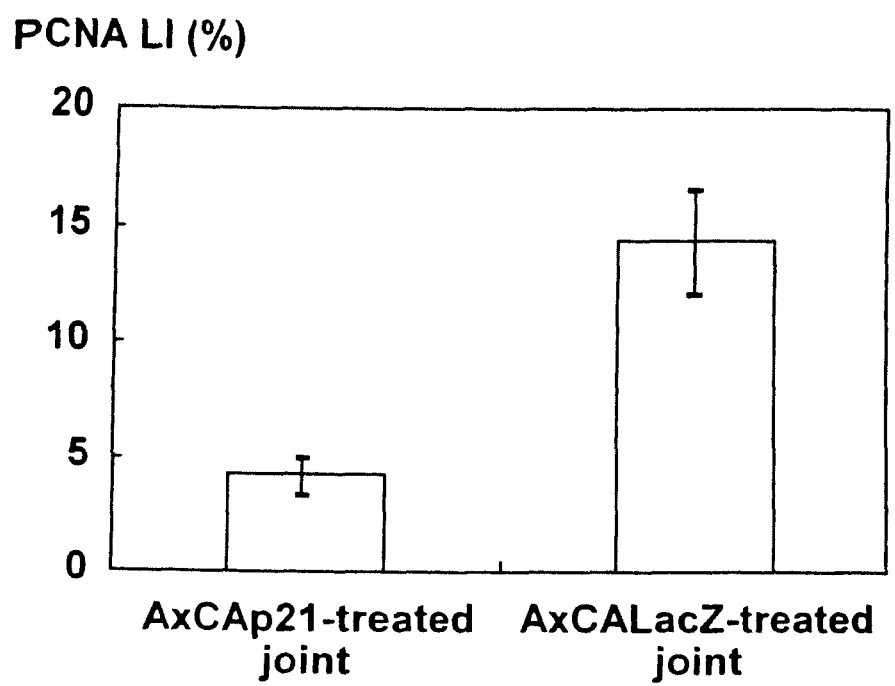

Synovial cells positive for PCNA staining were found more frequently in the synovial tissues of the AxCALacZ-administered joints than in those of the AxCAp21-administered joints (FIGS. 11A and B). The PCNA-labeling indices (LIs), which reflect frequency of the cells in the S phase, were calculated by examining three independent microscopic fields. They were significantly smaller in the AxCAp21-administered joints than in the AxCALacZ-administered joints (FIG. 11C). The result shows that the cell cycle of synovial cells was actually arrested in vivo.

Industrial Applicability

The present invention provides the p21$^{Cip1}$ protein, DNA encoding said protein, and compounds which increase the function or amount of p21$^{Cip1}$ protein for the inhibition of aberrant growth of synovial tissue, inflammation of synovial tissue, and/or the expression of inflammatory cytokines in synovial tissue. These molecules may be used as reagents for the inhibition of aberrant growth of synovial tissue, inflammation of synovial tissue, and/or the expression of inflammatory cytokines in synovial tissue. In addition, they are expected to be applicable as pharmaceutical compositions for the prevention or treatment of diseases related to aberrant growth of synovial tissue, inflammation of synovial tissue, and/or the express ion of inflammatory cytokines in synovial tissue, such as rheumatoid arthritis or the like.

The invention claimed is:

1. A method of reducing inflamed synovial tissue comprising:
   a) identifying a subject having inflamed synovial tissue in a joint; and
   b) administering an adenoviral vector encoding a protein consisting of a p21$^{Cip1}$ protein into the joint of the subject such that synovial tissue inflammation is reduced.

2. The method of claim 1, wherein the subject has rheumatoid arthritis.

3. The method of claim 1, wherein the method reduces growth of synovial tissue in the joint.

4. The method of claim 1, wherein the method reduces inflammatory cytokines in the joint.

5. The method of claim 1, wherein the method suppresses pannus formation in the joint.

6. The method of claim 1, wherein the method inhibits cartilage degeneration in the joint.

7. The method of claim 1, wherein the adenoviral vector is replication-defective.

8. The method of claim 1, wherein the p21$^{Cip1}$ protein is human p21$^{Cip1}$ protein.

9. The method of claim 1, wherein the subject is a human.

10. The method of claim 1, wherein the method reduces synovial thickening in the joint.

11. The method of claim 1, wherein the method reduces mononuclear cell infiltration in the joint.

12. A method of suppressing rheumatoid arthritis comprising:
   a) identifying a subject having rheumatoid arthritis in a joint; and
   b) administering an adenoviral vector encoding a protein consisting of a p21$^{Cip1}$ protein into the joint of the subject such that rheumatoid arthritis is suppressed.

13. The method of claim 12, wherein the subject is a human.

14. The method of claim 12, wherein the adenoviral vector is replication-defective.

15. The method of claim 12, wherein the p21$^{Cip1}$ protein is human p21$^{Cip1}$ protein.

* * * * *